(12) United States Patent
Davis et al.

(10) Patent No.: US 11,866,718 B2
(45) Date of Patent: Jan. 9, 2024

(54) PLANT REGULATORY ELEMENTS AND USES THEREOF

(71) Applicant: Monsanto Technology LLC, St. Louis, MO (US)

(72) Inventors: Ian W. Davis, Grover, MO (US); Aabid Shariff, Durham, NC (US)

(73) Assignee: MONSANTO TECHNOLOGY LLC, St. Louis, MO (US)

( * ) Notice: Subject to any disclaimer, the term of this patent is extended or adjusted under 35 U.S.C. 154(b) by 0 days.

(21) Appl. No.: 17/489,719

(22) Filed: Sep. 29, 2021

(65) Prior Publication Data
US 2022/0090110 A1 Mar. 24, 2022

Related U.S. Application Data

(63) Continuation of application No. 16/530,593, filed on Aug. 2, 2019, now Pat. No. 11,168,330.

(60) Provisional application No. 62/714,228, filed on Aug. 3, 2018.

(51) Int. Cl.
*C12N 15/82* (2006.01)

(52) U.S. Cl.
CPC ..... *C12N 15/8234* (2013.01); *C12N 15/8218* (2013.01)

(58) Field of Classification Search
None
See application file for complete search history.

(56) References Cited

U.S. PATENT DOCUMENTS

| 7,193,133 | B2 | 3/2007 | Lassner et al. | |
|---|---|---|---|---|
| 9,181,560 | B2 * | 11/2015 | Mroczka | C12N 15/8234 |
| 2011/0167514 | A1 | 7/2011 | Brover et al. | |
| 2016/0177326 | A1 | 6/2016 | Flaskinski | |

FOREIGN PATENT DOCUMENTS

WO 2014159434 10/2014

OTHER PUBLICATIONS

Genbank Accession No. X04753, dated Nov. 14, 2006.
Invitation to Pay Search Fees regarding PACT/2019-44845, dated Oct. 9, 2019, 2 pages.
International Search Report and Written Opinion regarding PCT Application No. PCT/US2019/044845, dated Dec. 4, 2019.
Kim et al., Plant Mol Biol 24: 105-117, 1994 (Year: 1994).
Aysha et al., Synthetic promoters: Designing the cis regulatory modules for controlled gene expression, Molecular Biotechnology 60: 608-620, 2018.
Extended European Search Report regarding European App. No. 19844807.8, dated Apr. 4, 2022.
Liu and Stewart, Plant synthetic promoters and transcription factors, Current Opinion in Biotechnology 37: 36-44, 2016.
Action regarding Colombia App. No. NC2020/0016038, dated Aug. 8, 2023.

* cited by examiner

*Primary Examiner* — Cynthia E Collins
(74) *Attorney, Agent, or Firm* — Dentons US LLP; Judith Koehler

(57) ABSTRACT

The invention provides recombinant DNA molecules and constructs, as well as their nucleotide sequences, useful for modulating gene expression in plants. The invention also provides transgenic plants, plant cells, plant parts, and seeds comprising the recombinant DNA molecules operably linked to heterologous transcribable DNA molecules, as are methods of their use.

17 Claims, No Drawings
Specification includes a Sequence Listing.

SEQUENCE LISTING

```
<160> NUMBER OF SEQ ID NOS: 26

<210> SEQ ID NO 1
<211> LENGTH: 500
<212> TYPE: DNA
<213> ORGANISM: Artificial
<220> FEATURE:
<223> OTHER INFORMATION: DNA sequence of the synthetic EXP, EXP-Zm.
      GSP850 comprising a synthetic promoter (P-Zm.GSP850.nno:4),
      operably linked 5' to a synthetic leader (L-Zm.GSP850.nno:3).
```

<400> SEQUENCE: 1

```
agacggcagc acaacggcca tccggtcgct gtaggtacac gagtgccgca gtagatggcg    60 cgcgttttg tctgagtccg atggagcagc gcagcgcccc cccccggcc accgccgctt     120 aggcggacag atcatcacgc cggccgccgg cctcatcgcc caaactgtgt ggcccaaaac    180
caccagacaa gcatattctg caggatgcc gttggcaaca aaaacacagg cgaccaaccc     240
aaacaggccg cccggcccat aaggagctcc gcaggcccat ttctcatttg gccaggatag    300
gccagccagg tggccacacg tgcaaaaccg ccacgtggcc aaggtggcgg atcccttatc    360
cacactggcc acacatgtgg cgccacacca caaccacaca ggcttatcta atagctgcta    420
tataaagagg aggagccgcc gcccaccacc actcaccagc acacaaaccc tagctgtttt    480
ccatcagaac cactcaccgg                                               500
```

<210> SEQ ID NO 2
<211> LENGTH: 450
<212> TYPE: DNA
<213> ORGANISM: Artificial
<220> FEATURE:
<223> OTHER INFORMATION: DNA sequence of a synthetic promoter, P-Zm.
GSP850.nno:4.

<400> SEQUENCE: 2

```
agacggcagc acaacggcca tccggtcgct gtaggtacac gagtgccgca gtagatggcg    60 cgcgttttg tctgagtccg atggagcagc gcagcgcccc cccccggcc accgccgctt     120 aggcggacag atcatcacgc cggccgccgg cctcatcgcc caaactgtgt ggcccaaaac    180
caccagacaa gcatattctg caggatgcc gttggcaaca aaaacacagg cgaccaaccc     240
aaacaggccg cccggcccat aaggagctcc gcaggcccat ttctcatttg gccaggatag    300
gccagccagg tggccacacg tgcaaaaccg ccacgtggcc aaggtggcgg atcccttatc    360
cacactggcc acacatgtgg cgccacacca caaccacaca ggcttatcta atagctgcta    420
tataaagagg aggagccgcc gcccaccacc                                    450
```

<210> SEQ ID NO 3
<211> LENGTH: 50
<212> TYPE: DNA
<213> ORGANISM: Artificial
<220> FEATURE:
<223> OTHER INFORMATION: DNA sequence of a synthetic leader, L-Zm.
GSP850.nno:3.

<400> SEQUENCE: 3

```
actcaccagc acacaaaccc tagctgtttt ccatcagaac cactcaccgg               50
```

<210> SEQ ID NO 4
<211> LENGTH: 1117
<212> TYPE: DNA
<213> ORGANISM: Artificial
<220> FEATURE:
<223> OTHER INFORMATION: DNA sequence of a synthetic EXP,
EXP-Zm.GSP850.nno+Zm.GSI153.nno:2 comprising a synthetic promoter
(P-Zm.GSP850.nno:4), a synthetic leader (L-Zm.GSP850.nno:3), and
a synthetic intron (I-Zm.GSI153.nno:1).

<400> SEQUENCE: 4

```
agacggcagc acaacggcca tccggtcgct gtaggtacac gagtgccgca gtagatggcg    60 cgcgttttg tctgagtccg atggagcagc gcagcgcccc cccccggcc accgccgctt     120 aggcggacag atcatcacgc cggccgccgg cctcatcgcc caaactgtgt ggcccaaaac    180
```

```
caccagacaa gcatattctg gcaggatgcc gttggcaaca aaaacacagg cgaccaaccc      240
aaacaggccg cccggcccat aaggagctcc gcaggcccat ttctcatttg gccaggatag      300
gccagccagg tggccacacg tgcaaaaccg ccacgtggcc aaggtggcgg atcccttatc      360
cacactggcc acacatgtgg cgccacacca caaccacaca ggcttatcta atagctgcta      420
tataaagagg aggagccgcc gcccaccacc actcaccagc acacaaaccc tagctgtttt      480
ccatcagaac cactcaccgg cggaccgctc aggtgagaac ctcgctcgtc tcccgcggat      540
ctgcttctcg taacggttcg atctgtgctg ctatttcgga ttcggatcta ctgcggtgcg      600
gttgacgatt taggtttgtt agggatctgg tggtcatgct tgatcgatct ggtcgattag      660
ggcccctcgc ggatctgcct tgttctgagt ttgggatctg gtgctcgaga tctcgatgcg      720
gattcgagag atctgctgca tcgatccgga tccggggttt cccatttgag cttctcctgc      780
cgccgccgct gtcttgccac tgactaggt agggtttccc cccgcgatct agcttcctgc      840
tggtactctc gccgaccgtc atccaaactc aaatttggcg gatccgacgc acatcgatct      900
gttgttcaca ctacaatcgt tgagtcgatg aggttattgt aaatctgatc tgggccgctg      960
cgattatccc tacctctctc ggaaacactg cgcgacgtgt aatatggtta aagtttgggc     1020
agttcgtagc gggttcggtc cctcggttct ggatttgagc tcccggtgga ttggtgtgtg     1080
tgctgttcta atgtattgat tcaatgttac aggttca                             1117

<210> SEQ ID NO 5
<211> LENGTH: 610
<212> TYPE: DNA
<213> ORGANISM: Artificial
<220> FEATURE:
<223> OTHER INFORMATION: DNA sequence of a synthetic intron, I-Zm.
      GSI153.nno:1.

<400> SEQUENCE: 5
ctcaggtgag aacctcgctc gtctcccgcg gatctgcttc tcgtaacggt tcgatctgtg       60
ctgctatttc ggattcggat ctactgcggt gcggttgacg atttaggttt gttagggatc      120
tggtggtcat gcttgatcga tctggtcgat tagggcccct cgcggatctg ccttgttctg      180
agtttgggat ctggtgctcg agatctcgat gcggattcga gagatctgct gcatcgatcc      240
ggatccgggg tttcccattt gagcttctcc tgccgccgcc gctgtcttgc cacctgacta      300
ggtagggttt ccccccgcga tctagcttcc tgctggtact ctcgccgacc gtcatccaaa      360
ctcaaatttg gcggatccga cgcacatcga tctgttgttc acactacaat cgttgagtcg      420
atgaggttat tgtaaatctg atctgggccg ctgcgattat ccctacctct ctcggaaaca      480
ctgcgcgacg tgtaatatgg ttaaagtttg gcagttcgt agcgggttcg gtccctcggt      540
tctggatttg agctcccggt ggattggtgt gtgtgctgtt ctaatgtatt gattcaatgt      600
tacaggttca                                                              610

<210> SEQ ID NO 6
<211> LENGTH: 500
<212> TYPE: DNA
<213> ORGANISM: Artificial
<220> FEATURE:
<223> OTHER INFORMATION: DNA sequence of a synthetic EXP, EXP-Zm.GSP990
      comprising a synthetic promoter (P-Zm.GSP990.nno:2), operably
      linked 5' to a synthetic leader (L-Zm.GSP990.nno:1).

<400> SEQUENCE: 6
gagaatgtgg gaggaacttg cgacagtaac ctcatttgg tcacaaaaac cgatatttaa        60
```

```
ggatcactag tcaccagacg aatctatttc atttgaacca tccaacgaga tgatctcaga    120
atgatccacg tcacaccaaa tttctcgtcg aactcggcca gcagagccat ccaaacgggg    180
atctccgcgc aacatctcca tccaccacct agagcagccc cggccttttc catggcaaaa    240
tttacatccg atttggctga agaccaatgg gaaaaaggcg ccacgtggcc acgtggcgtc    300
cacacgggcc aggcaggcag agaatggcca ccaatggggt ggataaggcc ggcgccaaaa    360
atatctgcca cgtggcgcct tgtggataag gcagcttgct atccctccgc caatcctata    420
tatatccttt cccctctcct agtgccgctc aaagctaagc acaacctaag ctgatccact    480
gcaagcatcg tctcctacta                                                500

<210> SEQ ID NO 7
<211> LENGTH: 450
<212> TYPE: DNA
<213> ORGANISM: Artificial
<220> FEATURE:
<223> OTHER INFORMATION: DNA sequence of a synthetic promoter, P-Zm.
      GSP990.nno:2.

<400> SEQUENCE: 7
gagaatgtgg gaggaacttg cgacagtaac ctcattttgg tcacaaaaac cgatatttaa     60
ggatcactag tcaccagacg aatctatttc atttgaacca tccaacgaga tgatctcaga    120
atgatccacg tcacaccaaa tttctcgtcg aactcggcca gcagagccat ccaaacgggg    180
atctccgcgc aacatctcca tccaccacct agagcagccc cggccttttc catggcaaaa    240
tttacatccg atttggctga agaccaatgg gaaaaaggcg ccacgtggcc acgtggcgtc    300
cacacgggcc aggcaggcag agaatggcca ccaatggggt ggataaggcc ggcgccaaaa    360
atatctgcca cgtggcgcct tgtggataag gcagcttgct atccctccgc caatcctata    420
tatatccttt cccctctcct agtgccgctc                                     450

<210> SEQ ID NO 8
<211> LENGTH: 50
<212> TYPE: DNA
<213> ORGANISM: Artificial
<220> FEATURE:
<223> OTHER INFORMATION: DNA sequence of a synthetic leader, L-Zm.
      GSP990.nno:1.

<400> SEQUENCE: 8
aaagctaagc acaacctaag ctgatccact gcaagcatcg tctcctacta                50

<210> SEQ ID NO 9
<211> LENGTH: 1117
<212> TYPE: DNA
<213> ORGANISM: Artificial
<220> FEATURE:
<223> OTHER INFORMATION: DNA sequence of a synthetic EXP,
      EXP-Zm.GSP990.nno+Zm.GSI197.nno:2 comprising a synthetic promoter
      (P-Zm.GSP990.nno:2), a synthetic leader (L-Zm.GSP990.nno:1), and
      a synthetic intron (I-Zm.GSI197.nno:1).

<400> SEQUENCE: 9
gagaatgtgg gaggaacttg cgacagtaac ctcattttgg tcacaaaaac cgatatttaa     60
ggatcactag tcaccagacg aatctatttc atttgaacca tccaacgaga tgatctcaga    120
atgatccacg tcacaccaaa tttctcgtcg aactcggcca gcagagccat ccaaacgggg    180
atctccgcgc aacatctcca tccaccacct agagcagccc cggccttttc catggcaaaa    240
tttacatccg atttggctga agaccaatgg gaaaaaggcg ccacgtggcc acgtggcgtc    300
```

```
cacacgggcc aggcaggcag agaatggcca ccaatggggt ggataaggcc ggcgccaaaa      360
atatctgcca cgtggcgcct tgtggataag gcagcttgct atccctccgc caatcctata      420
tatatccttt ccctctcct agtgccgctc aaagctaagc acaacctaag ctgatccact       480
gcaagcatcg tctcctacta cggaccgtac aggtaagcga gcgccgctcg ctcccgccgt      540
ctcccttctc tgccggatct gccgtgctgc cgtcgtggcg tccatcctga tctccctccc     600
atcgacccct cggccgggcg gtttctgttt tatagggttt cctcccacc tcgcgggcag       660
tttgctgctg cctgctcaga tcccagctgg ttggatctgc ggattcgggt aggcggattc      720
gccgggccga gttatataaa ccatttactg tagatgcgtt actaccttaa tgacgcacgg     780
atctgccgtc tcgcccccccc ccgcgtcgga tccgactgtt agcttcctgc cacggatctg    840
ctggactgtt ttcttgatcg ggtcttgcat ttggtggtgg cgggaatata ttatttaga     900
tggtctgggt ctgcggatcc gtgcttattt tgttaccatg cccccacctg actataaact     960
gtaaggtcga tctgatttgt ttgctatgcc cctcttgccg tctggatatg atggaaatat   1020
atccgatcca gatgatgcta gtctctccct cgagcttctc gagggggtcg atctgaagtc   1080
agttctaatt aatattttga tgctgattac aggtagc                             1117

<210> SEQ ID NO 10
<211> LENGTH: 610
<212> TYPE: DNA
<213> ORGANISM: Artificial
<220> FEATURE:
<223> OTHER INFORMATION: DNA sequence of a synthetic intron, I-Zm.
      GSI197.nno:1.

<400> SEQUENCE: 10
tacaggtaag cgagcgccgc tcgctcccgc cgtctccctt ctctgccgga tctgccgtgc     60
tgccgtcgtg gcgtccatcc tgatctccct cccatcgacc cctcggccgg gcggtttctg   120
ttttataggg tttccctccc acctcgcggg cagtttgctg ctgcctgctc agatcccagc   180
tggttggatc tgcggattcg ggtaggcgga ttcgccgggc cgagttatat aaaccattta   240
ctgtagatgc gttactacct taatgacgca cggatctgcc gtctcgcccc ccccgcgtc    300
ggatccgact gttagcttcc tgccacggat ctgctggact gttttcttga tcgggtcttg   360
catttggtgg tggcgggaat atattatttt agatggtctg ggtctgcgga tccgtgctta   420
ttttgttacc atgcccccac tgactataa actgtaaggt cgatctgatt tgtttgctat    480
gcccctcttg ccgtctggat atgatggaaa tatatccgat ccagatgatg ctagtctctc   540
cctcgagctt ctcgaggggg tcgatctgaa gtcagttcta attaatatttt tgatgctgat   600
tacaggtagc                                                          610

<210> SEQ ID NO 11
<211> LENGTH: 1117
<212> TYPE: DNA
<213> ORGANISM: Artificial
<220> FEATURE:
<223> OTHER INFORMATION: DNA sequence of a synthetic EXP,
      EXP-Zm.GSP850.nno+Zm.GSI140.nno:1 comprising a synthetic promoter
      (P-Zm.GSP850.nno:4), a synthetic leader (L-Zm.GSP850.nno:3), and
      a synthetic intron (I-Zm.GSI140.nno:1).

<400> SEQUENCE: 11
agacggcagc acaacggcca tccggtcgct gtaggtacac gagtgccgca gtagatggcg      60
cgcgttttttg tctgagtccg atggagcagc gcagcgcccc ccccccggcc accgccgctt    120
```

| | |
|---|---|
| aggcggacag atcatcacgc cggccgccgg cctcatcgcc caaactgtgt ggcccaaaac | 180 |
| caccagacaa gcatattctg gcaggatgcc gttggcaaca aaaacacagg cgaccaaccc | 240 |
| aaacaggccg cccggcccat aaggagctcc gcaggcccat ttctcatttg gccaggatag | 300 |
| gccagccagg tggccacacg tgcaaaaccg ccacgtggcc aaggtggcgg atcccttatc | 360 |
| cacactggcc acacatgtgg cgccacacca caaccacaca ggcttatcta atagctgcta | 420 |
| tataaagagg aggagccgcc gcccaccacc actcaccagc acacaaaccc tagctgtttt | 480 |
| ccatcagaac cactcaccgg cggaccggcc aggtacgcct cctcctccgc gccgctcttc | 540 |
| ctgcccaccc cgctcgatct gccacggatc cgctcggatc tggtccccctt cgattcggcc | 600 |
| acgatcggat ccgccgccgg gcgctcgcca tcggtggtgt ggtggctgta ggtttgcgtc | 660 |
| gtaagtttcc tgctccctcg ctggatgctt ccttctagcg gattcggcga cccatttctc | 720 |
| gcccgacggt cttccctctc tcttggctcg caaatcagga tgggtgttgt ttgatgctgt | 780 |
| catcgcccgt ttgatccgtc tcaaaattgc tctcccccgc gcacggatcg atctgctccc | 840 |
| cctctctgct ccctgacccc gtctcacggc ggcgcgccgc tgctgctgct gtgccattcc | 900 |
| atcagtcata caatcggagt aggcggaaat ataaaaatcg tccccttagc agcagatgga | 960 |
| tccgtccatt tccggattcg agtcgattcg tgtgctcccc cctctctct cgcccggatc | 1020 |
| tgattgcgac aacttgcttc tcccctccat ttcgatcccc atgtttacga tacttttccc | 1080 |
| aactaatatt gatgtgggtg actgttttac aggtttc | 1117 |

<210> SEQ ID NO 12
<211> LENGTH: 610
<212> TYPE: DNA
<213> ORGANISM: Artificial
<220> FEATURE:
<223> OTHER INFORMATION: DNA sequence of a synthetic intron, I-Zm.
      GSI140.nno:1.

<400> SEQUENCE: 12

| | |
|---|---|
| gccaggtacg cctcctcctc cgcgccgctc ttcctgccca ccccgctcga tctgccacgg | 60 |
| atccgctcgg atctggtccc cttcgattcg gccacgatcg gatccgccgc cgggcgctcg | 120 |
| ccatcggtgg tgtggtggct gtaggtttgc gtcgtaagtt tcctgctccc tcgctggatg | 180 |
| cttccttcta gcggattcgg cgacccattt ctcgcccgac ggtcttccct ctctcttggc | 240 |
| tcgcaaatca ggatgggtgt tgtttgatgc tgtcatcgcc cgtttgatcc gtctcaaaat | 300 |
| tcgtctcccc cgcgcacgga tcgatctgct ccccctctct gctccctgac ccgtctcac | 360 |
| ggcggcgcgc cgctgctgct gctgtgccat tccatcagtc atacaatcgg agtaggcgga | 420 |
| aatataaaaa tcgtcccctt agcagcagat ggatccgtcc atttccggat tcgagtcgat | 480 |
| tcgtgtgctc cccccctctc tctcgcccgg atctgattgc gacaacttgc ttctcccctc | 540 |
| catttcgatc cccatgttta cgatactttt cccaactaat attgatgtgg gtgactgttt | 600 |
| tacaggtttc | 610 |

<210> SEQ ID NO 13
<211> LENGTH: 300
<212> TYPE: DNA
<213> ORGANISM: Artificial
<220> FEATURE:
<223> OTHER INFORMATION: DNA sequence of the synthetic 3' UTR, T-Zm.
      GST9.nno:2.

<400> SEQUENCE: 13

| | |
|---|---|
| gtcgtcgtgg ttttttttgt ttttgtatct gaaggaggcc gccccatgtg tgttgttgta | 60 |

```
gctagcagaa gaaggccacc gttcctgtac attttgttgt gctgctgctg cttgttcttc    120
gtggatgtac atttgtatca tgttttttg gttgtaaact ctatataaga aatgaataag     180
taataaagaa gttgtttcat acccggtgct tccttgtttg ttgtgatatc ttttggctag    240
cttccttgtt aaccatgaaa tatatggccg tcggcatcat ttttgtttg tcttattttc     300
```

<210> SEQ ID NO 14
<211> LENGTH: 400
<212> TYPE: DNA
<213> ORGANISM: Artificial
<220> FEATURE:
<223> OTHER INFORMATION: DNA sequence of the synthetic 3' UTR, T-Zm.
    GST18.nno:2.

<400> SEQUENCE: 14

```
tgctctacca agtagttgtg tgtgctgtcg atccatcttg ctgctgctac atgcatgttt     60
ttgagcaggt ggtttctttt ggtttcgact ggttgttttg taaactatca ctatatatta   120
aataaatgga ataaagttgt ttttctcat accaagttcg tgctgtgttc tgatgccgcc    180
gctgtttggt ttgctcatgc tgtgtggttg tttcttgatt ttttggttc ctgtgtagct    240 gcagtttgtt ttgaatctac ctagcatgtg tgatatgttt gctgcgtcgg caaccttgta   300
aactttggtt tcacgatgaa ataaattaat aaatattttg gttttctcat accgtgcttg   360
caaggatgtt tgtttgtttc ggtattcccc tgcatatttt                          400
```

<210> SEQ ID NO 15
<211> LENGTH: 1311
<212> TYPE: DNA
<213> ORGANISM: Artificial
<220> FEATURE:
<223> OTHER INFORMATION: DNA sequence of a synthetic EXP, EXP-Zm.GSP850.
    nno+Zm.DnaK:1 comprising a synthetic promoter (P-Zm.GSP850.nno:4),
    operably linked 5' to a synthetic leader (L-Zm.GSP850.nno:3),
    operably linked 5' to an intron (I-Zm.DnaK:1).

<400> SEQUENCE: 15

```
agacggcagc acaacggcca tccggtcgct gtaggtacac gagtgccgca gtagatggcg     60 cgcgttttg tctgagtccg atggagcagc gcagcgcccc ccccccggcc accgccgctt    120
aggcggacag atcatcacgc cggccgccgg cctcatcgcc caaactgtgt ggcccaaaac    180
caccagacaa gcatattctg gcaggatgcc gttggcaaca aaaacacagg cgaccaaccc    240
aaacaggccg cccggcccat aaggagctcc gcaggcccat ttctcatttg gccaggatag    300
gccagccagt tggccacacg tgcaaaaccg ccacgtggcc aaggtggcgg atcccttatc    360
cacactggcc acacatgtgg cgccacacca caaccacaca ggcttatcta atagctgcta    420
tataaagagg aggagccgcc gcccaccacc actcaccagc acacaaaccc tagctgtttt    480
ccatcagaac cactcaccgg cggaccgacc gtcttcggta cgcgctcact ccgccctctg    540
cctttgttac tgccacgttt ctctgaatgc tctcttgtgt ggtgattgct gagagtggtt    600
tagctggatc tagaattaca ctctgaaatc gtgttctgcc tgtgctgatt acttgccgtc    660
ctttgtagca gcaaaatata gggacatggt agtacgaaac gaagatagaa cctacacagc    720
aatacgagaa atgtgtaatt tggtgcttag cggtatttat ttaagcacat gttggtgtta    780
tagggcactt ggattcagaa gtttgctgtt aatttaggca caggcttcat actacatggg    840
tcaatagtat agggattcat attataggcg atactataat aatttgttcg tctgcagagc    900
ttattatttg ccaaaattag atattcctat tctgtttttg tttgtgtgct gttaaattgt    960
```

```
taacgcctga aggaataaat ataaatgacg aaatttttgat gtttatctct gctcctttat    1020
tgtgaccata agtcaagatc agatgcactt gttttaaata ttgttgtctg aagaaataag    1080
tactgacagt attttgatgc attgatctgc ttgtttgttg taacaaaatt taaaaataaa    1140
gagtttcctt tttgttgctc tccttacctc ctgatggtat ctagtatcta ccaactgaca    1200
ctatattgct tctctttaca tacgtatctt gctcgatgcc ttctccctag tgttgaccag    1260
tgttactcac atagtctttg ctcatttcat tgtaatgcag ataccaagcg g             1311
```

<210> SEQ ID NO 16
<211> LENGTH: 1311
<212> TYPE: DNA
<213> ORGANISM: Artificial
<220> FEATURE:
<223> OTHER INFORMATION: DNA sequence of a synthetic EXP, EXP-Zm.GSP990.
   nno+Zm.DnaK:1 comprising a synthetic promoter (P-Zm.GSP990.nno:2),
   operably linked 5' to a synthetic leader (L-Zm.GSP990.nno:1),
   operably linked 5' to an intron (I-Zm.DnaK:1).

<400> SEQUENCE: 16

```
gagaatgtgg gaggaacttg cgacagtaac ctcattttgg tcacaaaaac cgatatttaa     60
ggatcactag tcaccagacg aatctatttc atttgaacca tccaacgaga tgatctcaga    120
atgatccacg tcacaccaaa tttctcgtcg aactcggcca gcagagccat ccaaacgggg    180
atctccgcgc aacatctcca tccaccacct agagcagccc cggccttttc catggcaaaa    240
tttacatccg atttggctga agaccaatgg gaaaaaggcg ccacgtggcc acgtggcgtc    300
cacacgggcc aggcaggcag agaatggcca ccaatggggt ggataaggcc ggcgccaaaa    360
atatctgcca cgtggcgcct tgtggataag gcagcttgct atccctccgc caatcctata    420
tatatccttt cccctctcct agtgccgctc aaagctaagc acaacctaag ctgatccact    480
gcaagcatcg tctcctacta cggaccgacc gtcttcggta cgcgctcact ccgccctctg    540
cctttgttac tgccacgttt ctctgaatgc tctcttgtgt ggtgattgct gagagtggtt    600
tagctggatc tagaattaca ctctgaaatc gtgttctgcc tgtgctgatt acttgccgtc    660
ctttgtagca gcaaaatata gggacatggt agtacgaaac gaagatagaa cctacacagc    720
aatacgagaa atgtgtaatt tggtgctag cggtatttat ttaagcacat gttggtgtta    780
tagggcactt ggattcagaa gttttgctgtt aatttaggca caggcttcat actacatggg    840
tcaatagtat agggattcat attataggcg atactataat aatttgttcg tctgcagagc    900
ttattatttg ccaaaattag atattcctat tctgtttttg tttgtgtgct gttaaattgt    960
taacgcctga aggaataaat ataaatgacg aaatttttgat gtttatctct gctcctttat   1020
tgtgaccata agtcaagatc agatgcactt gttttaaata ttgttgtctg aagaaataag   1080
tactgacagt attttgatgc attgatctgc ttgtttgttg taacaaaatt taaaaataaa   1140
gagtttcctt tttgttgctc tccttacctc ctgatggtat ctagtatcta ccaactgaca   1200
ctatattgct tctctttaca tacgtatctt gctcgatgcc ttctccctag tgttgaccag   1260
tgttactcac atagtctttg ctcatttcat tgtaatgcag ataccaagcg g            1311
```

<210> SEQ ID NO 17
<211> LENGTH: 418
<212> TYPE: DNA
<213> ORGANISM: Artificial
<220> FEATURE:
<223> OTHER INFORMATION: DNA sequence of a synthetic enhancer, E-Zm.
   GSP850 which is derived from the synthetic promoter, P-Zm.GSP850.
   nno:4.

<400> SEQUENCE: 17

```
agacggcagc acaacggcca tccggtcgct gtaggtacac gagtgccgca gtagatggcg      60
cgcgttttg tctgagtccg atggagcagc gcagcgcccc cccccggcc accgccgctt      120
aggcggacag atcatcacgc cggccgccgg cctcatcgcc caaactgtgt ggcccaaaac      180
caccagacaa gcatattctg caggatgcc gttggcaaca aaaacacagg cgaccaaccc       240
aaacaggccg cccggcccat aaggagctcc gcaggcccat ttctcatttg gccaggatag      300
gccagccagg tggccacacg tgcaaaaccg ccacgtggcc aaggtggcgg atcccttatc      360
cacactggcc acacatgtgg cgccacacca caaccacaca ggcttatcta atagctgc       418
```

<210> SEQ ID NO 18
<211> LENGTH: 416
<212> TYPE: DNA
<213> ORGANISM: Artificial
<220> FEATURE:
<223> OTHER INFORMATION: DNA sequence of a synthetic enhancer, E-Zm.
    GSP990 which is derived from the synthetic promoter, P-Zm.
    GSP990.nno:2.

<400> SEQUENCE: 18

```
gagaatgtgg gaggaacttg cgacagtaac ctcatttttgg tcacaaaaac cgatatttaa      60
ggatcactag tcaccagacg aatctatttc atttgaacca tccaacgaga tgatctcaga     120
atgatccacg tcacaccaaa tttctcgtcg aactcggcca gcagagccat ccaaacgggg     180
atctccgcgc aacatctcca tccaccacct agagcagccc cggccttttc catggcaaaa     240
tttacatccg atttggctga agaccaatgg gaaaaaggcg ccacgtggcc acgtggcgtc     300
cacacgggcc aggcaggcag agaatggcca ccaatggggt ggataaggcc ggcgccaaaa     360
atatctgcca cgtggcgcct tgtggataag gcagcttgct atccctccgc caatcc        416
```

<210> SEQ ID NO 19
<211> LENGTH: 487
<212> TYPE: DNA
<213> ORGANISM: Sorghum bicolor
<220> FEATURE:
<221> NAME/KEY: misc_feature
<222> LOCATION: (1)..(487)
<223> OTHER INFORMATION: DNA sequence of a 3' UTR, T-Sb.Nltp4-1:1:2
    derived from the NLTP4 (non-specific lipid-transfer protein 4)
    gene from Sorghum bicolor.

<400> SEQUENCE: 19

```
tgatcgatca taaggacatg catgaggcat gctcgttgga tggcgatcag catgcagtcg      60
tcgttgtttt accagatgtc gtccatgact ccctccatgg atgatgcatg caatgagata     120
gatacataaa ttaaggagta gatcatgcat gcaccgtacc tgttagtgat cactccgttt     180
aattagtatt tactgtttac taccttgagt ttacaccaac tctgtcgtcg ctgtggctgt     240
cgtcgtgtac ctcgatcgta cgtgtgtgtg tgtagcaggc tagcaaagca gcactcaacg     300
tcgtccttgg gggtttgctt gcctttaacc ttgttgcttt agcacacagg ttctgaata       360
atgaatacta ctagcttttg tgtccattat atatatattg tactgtatgc atgatgtttt      420
ccatccatga gtcatgagag tgatgtgttc aagtaataag atatagtaac atatacacgc     480
gacgtac                                                               487
```

<210> SEQ ID NO 20
<211> LENGTH: 2001
<212> TYPE: DNA
<213> ORGANISM: Artificial -continued

```
<220> FEATURE:
<223> OTHER INFORMATION: Synthetic coding sequence optimized for plant
      expression for Beta-glucuronidase (GUS) with a processable intron
      derived from the potato light-inducible tissue-specific ST-LS1
      gene (Genbank Accession: X04753).

<400> SEQUENCE: 20
atggtgaggc cgttgagac  cccgactagg gagatcaaga agctggacgg cctctgggcc      60
ttctccctcg accgtgagaa ctgcggcatc gaccagcgct ggtgggagtc cgccctccag     120
gagtctaggg ccatcgccgt gcccggttcc ttcaacgacc agttcgccga cgccgacatc     180
cgcaactacg cgggcaacgt ctggtatcag cgcgaggtgt tcatcccgaa gggctgggcg     240
ggccagcgca tcgtgctccg cttcgacgcc gtgacccact acggcaaggt ctgggtgaac     300
aatcaggagg taagtttctg cttctacctt tgatatatat ataataatta tcattaatta     360
gtagtaatat aatatttcaa atatttttt  caaaataaaa gaatgtagta tatagcaatt     420
gcttttctgt agtttataag tgtgtatatt ttaatttata acttttctaa tatatgacca     480
aaatttgttg atgtgcaggt gatggagcac cagggcggtt acaccccgtt cgaggccgac     540
gtgacgccgt acgtgatcgc cgggaagtcc gtccgcatca ccgtctgcgt gaacaatgag     600
ctgaactggc agaccatccc gcctggcatg gtcatcaccg acgagaacgg caagaagaag     660
cagtcctact ccacgactt  cttcaactac gctggcatcc accgctccgt gatgctctac     720
accactccca cacctgggt  ggacgacatc accgtggtca cccacgtggc ccaggactgc     780
aaccacgcct ccgtggactg gcaagtcgtt gccaacggcg acgtcagcgt cgagctgcgc     840
gacgccgacc agcaagtcgt tgccaccggc cagggcacca gcggcaccct caagtcgtc      900
aaccctcacc tctggcagcc tggcgagggc tacctctacg agctgtgcgt caccgccaag     960
agccagactg agtgcgacat ctaccctctc cgcgtcggca tcaggagcgt cgctgtcaag    1020
ggcgagcagt tcctcatcaa ccacaagcct ttctacttca ctggtttcgg ccgccacgag    1080
gacgctgacc tgaggggcaa gggtttcgac aacgtcctga tggtccacga ccacgctctg    1140
atggactgga tcggtgccaa cagctacagg accagtcact acccgtacgc tgaggagatg    1200
ctggactggg ctgacgagca cggtatcgtc gtgatcgacg agactgctgc ggtcggtttc    1260
aacctgtctc tgggcattgg tttcgaggct gggaacaagc cgaaggagct gtactctgag    1320
gaagctgtca acggcgagac tcagcaagct catctccagg cgattaagga gctgattgcc    1380
agggacaaga accatccgtc tgtcgtgatg tggtctattg cgaatgagcc ggacaccaga    1440
ccgcaagggg cgcgtgaata cttcgcgccg ctggcggagg cgactcgcaa actggaccca    1500
acccgtccaa tcacgtgcgt caatgtcatg ttctgcgacg cccatacgga tacgatctcg    1560
gacctgttcg atgttctttg tctcaatcgg tactatgggt ggtatgttca gagcggggat    1620
cttgagacgg cggagaaggt tcttgagaag gaactcctgg cgtggcaaga gaagctccat    1680
cagccgatca ttatcacgga gtacgggtt  gacacacttg cgggccttca cagtatgtac    1740
acagatatgt ggtcggagga ataccagtgt gcatggttgg atatgtacca tcgtgtcttc    1800
gaccgggttt cagcggttgt cggcgaacaa gtctggaact tcgcagactt cgccacgagc    1860
caagggatac tgcgggtagg agggaacaag aagggaatct tcacacggga tcggaagccc    1920
aagtcagcag ccttcctgtt gcagaagcga tggacaggaa tgaacttcgg agaaaagcca    1980
cagcaaggcg gaaagcagtg a                                              2001

<210> SEQ ID NO 21
<211> LENGTH: 835
```

```
<212> TYPE: DNA
<213> ORGANISM: Cauliflower mosaic virus
<220> FEATURE:
<221> NAME/KEY: misc_feature
<222> LOCATION: (1)..(835)
<223> OTHER INFORMATION: DNA sequence of the EXP, EXP-CaMV.35S
      comprising the 35S promoter and leader derived from the
      Cauliflower mosaic virus.

<400> SEQUENCE: 21
agattagcct tttcaatttc agaaagaatg ctaacccaca gatggttaga gaggcttacg    60
cagcaggtct catcaagacg atctacccga gcaataatct ccaggaaatc aaataccttc   120
ccaagaaggt taaagatgca gtcaaaagat tcaggactaa ctgcatcaag aacacagaga   180
aagatatatt tctcaagatc agaagtacta ttccagtatg gacgattcaa ggcttgcttc   240
acaaaccaag gcaagtaata gagattggag tctctaaaaa ggtagttccc actgaatcaa   300
aggccatgga gtcaaagatt caaatagagg acctaacaga actcgccgta aagactggcg   360
aacagttcat acagagtctc ttacgactca atgacaagaa gaaaatcttc gtcaacatgg   420
tggagcacga cacacttgtc tactccaaaa atatcaaaga tacagtctca gaagaccaaa   480
gggcaattga ctttttcaa caaagggtaa tatccggaaa cctcctcgga ttccattgcc   540
cagctatctg tcactttatt gtgaagatag tggaaaagga aggtggctcc tacaaatgcc   600
atcattgcga taaaggaaag gccatcgttg aagatgcctc tgccgacagt ggtcccaaag   660 atggacccc acccacgagg agcatcgtgg aaaaagaaga cgttccaacc acgtcttcaa   720
agcaagtgga ttgatgtgat atctccactg acgtaaggga tgacgcacaa tcccactatc   780
cttcgcaaga cccttcctct ataaggaa gttcatttca tttggagagg acacg          835

<210> SEQ ID NO 22
<211> LENGTH: 804
<212> TYPE: DNA
<213> ORGANISM: Zea mays
<220> FEATURE:
<221> NAME/KEY: misc_feature
<222> LOCATION: (1)..(804)
<223> OTHER INFORMATION: DNA sequence of the intron, I-Zm.DnaK:1 derived
      from the heat shock protein 70 (Hsp70) gene (DnaK) from Zea mays.

<400> SEQUENCE: 22
accgtcttcg gtacgcgctc actccgccct ctgcctttgt tactgccacg tttctctgaa    60
tgctctcttg tgtggtgatt gctgagagtg gtttagctgg atctagaatt acactctgaa   120
atcgtgttct gcctgtgctg attacttgcc gtcctttgta gcagcaaaat atagggacat   180
ggtagtacga aacgaagata gaacctacac agcaatacga gaaatgtgta atttggtgct   240
tagcggtatt tatttaagca catgttggtg ttatagggca cttggattca gaagtttgct   300
gttaatttag gcacaggctt catactacat gggtcaatag tatagggatt catattatag   360
gcgatactat aataatttgt tcgtctgcag agcttattat ttgccaaaat tagatattcc   420
tattctgttt ttgtttgtgt gctgttaaat tgttaacgcc tgaaggaata aatataaatg   480
acgaaatttt gatgtttatc tctgctcctt tattgtgacc ataagtcaag atcagatgca   540
cttgttttaa atattgttgt ctgaagaaat aagtactgac agtatttga tgcattgatc    600 tgcttgtttg ttgtaacaaa atttaaaaat aaagagtttc cttttgttg ctctccttac    660 ctcctgatgg tatctagtat ctaccaactg acactatatt gcttctcttt acatacgtat   720
cttgctcgat gccttctccc tagtgttgac cagtgttact cacatagtct ttgctcattt   780
cattgtaatg cagataccaa gcgg                                          804
```

<210> SEQ ID NO 23
<211> LENGTH: 300
<212> TYPE: DNA
<213> ORGANISM: Oryza sativa
<220> FEATURE:
<221> NAME/KEY: misc_feature
<222> LOCATION: (1)..(300)
<223> OTHER INFORMATION: DNA sequence of a 3' UTR, T-Os.LTP:1 derived from the Lipid Transfer Protein-like gene (LTP) from Oryza sativa.

<400> SEQUENCE: 23

```
attaatcgat cctccgatcc cttaattacc ataccattac accatgcatc aatatccata      60
tatatataaa cccttttcgca cgtacttata ctatgttttg tcatacatat atatgtgtcg     120
aacgatcgat ctatcactga tatgatatga ttgatccatc agcctgatct ctgtatcttg     180
ttatttgtat accgtcaaat aaaagtttct tccacttgtg ttaataatta gctactctca     240
tctcatgaac cctatatata actagtttaa tttgctgtca attgaacatg atgatcgatg     300
```

<210> SEQ ID NO 24
<211> LENGTH: 2001
<212> TYPE: DNA
<213> ORGANISM: Artificial
<220> FEATURE:
<223> OTHER INFORMATION: Coding sequence for Beta-glucuronidase (GUS) with a processable intron derived from the potato light-inducible tissue-specific ST-LS1 gene (Genbank Accession: X04753).

<400> SEQUENCE: 24

```
atggtccgtc ctgtagaaac cccaacccgt gaaatcaaaa aactcgacgg cctgtgggca      60
ttcagtctgg atcgcgaaaa ctgtggaatt gatcagcgtt ggtgggaaag cgcgttacaa     120
gaaagccggg caattgctgt gccaggcagt tttaacgatc agttcgccga tgcagatatt     180
cgtaattatg cgggcaacgt ctggtatcag cgcgaagtct ttataccgaa aggttgggca     240
ggccagcgta tcgtgctgcg tttcgatgcg gtcactcatt acggcaaagt gtgggtcaat     300
aatcaggaag tgatggagca tcagggcggc tatacgccat ttgaagccga tgtcacgccg     360
tatgttattg ccgggaaaag tgtacgtaag tttctgcttc tacctttgat atatatataa     420
taattatcat taattagtag taatataata tttcaaatat ttttttcaaa ataaaagaat     480
gtagtatata gcaattgctt ttctgtagtt tataagtgtg tatattttaa tttataactt     540
ttctaatata tgaccaaaat tgttgatgt gcaggtatca ccgtttgtgt gaacaacgaa     600
ctgaactggc agactatccc gccgggaatg gtgattaccg acgaaaacgg caagaaaaag     660
cagtcttact tccatgattt ctttaactat gccggaatcc atcgcagcgt aatgctctac     720
accacgccga acacctgggt ggacgatatc accgtggtga cgcatgtcgc gcaagactgt     780
aaccacgcgt ctgttgactg caggtggtg gccaatggtg atgtcagcgt tgaactgcgt     840
gatgcggatc aacaggtggt tgcaactgga caaggcacta gcgggacttt gcaagtggtg     900
aatccgcacc tctggcaacc gggtgaaggt tatctctatg aactgtgcgt cacagccaaa     960
agccagacag agtgtgatat ctacccgctt cgcgtcggca tccggtcagt ggcagtgaag    1020
ggcgaacagt tcctgattaa ccacaaaccg ttctacttta ctggctttgg tcgtcatgaa    1080
gatgcggact tgcgtggcaa aggattcgat aacgtgctga tggtgcacga ccacgcatta    1140
atggactgga ttggggccaa ctcctaccgt acctcgcatt accctacgc tgaagagatg    1200
ctcgactggg cagatgaaca tggcatcgtg gtgattgatg aaactgctgc tgtcggcttt    1260
aacctctctt taggcattgg tttcgaagcg ggcaacaagc cgaaagaact gtacagcgaa    1320
```

```
gaggcagtca acgggaaac tcagcaagcg cacttacagg cgattaaaga gctgatagcg      1380
cgtgacaaaa accacccaag cgtggtgatg tggagtattg ccaacgaacc ggatacccgt      1440
ccgcaaggtg cacgggaata tttcgcgcca ctggcggaag caacgcgtaa actcgacccg      1500
acgcgtccga tcacctgcgt caatgtaatg ttctgcgacg ctcacaccga taccatcagc      1560
gatctctttg atgtgctgtg cctgaaccgt tattacggat ggtatgtcca agcggcgat       1620 ttggaaacgg cagagaaggt actggaaaaa gaacttctgg cctggcagga gaaactgcat      1680
cagccgatta tcatcaccga atacggcgtg gatacgttag ccgggctgca ctcaatgtac      1740
accgacatgt ggagtgaaga gtatcagtgt gcatggctgg atatgtatca ccgcgtcttt      1800
gatcgcgtca gcgccgtcgt cggtgaacag gtatggaatt cgccgatttt gcgacctcg      1860 caaggcatat tgcgcgttgg cggtaacaag aaagggatct tcactcgcga ccgcaaaccg      1920
aagtcggcgg cttttctgct gcaaaaacgc tggactggca tgaacttcgg tgaaaaaccg      1980
cagcagggag gcaaacaatg a                                                2001
```

<210> SEQ ID NO 25
<211> LENGTH: 516
<212> TYPE: DNA
<213> ORGANISM: Artificial
<220> FEATURE:
<223> OTHER INFORMATION: Coding sequence for Nluc, a luciferase protein
      engineered by directed evolution.

<400> SEQUENCE: 25

```
atggtcttca cactcgaaga tttcgttggg gactggcgac agacagccgg ctacaacctg      60
gaccaagtcc ttgaacaggg aggtgtgtcc agtttgtttc agaatctcgg ggtgtccgta     120
actccgatcc aaaggattgt cctgagcggt gaaaatgggc tgaagatcga catccatgtc     180
atcatcccgt atgaaggtct gagcggcgac caaatgggcc agatcgaaaa aatttttaag     240
gtggtgtacc ctgtggatga tcatcacttt aaggtgatcc tgcactatgg cacactggta     300
atcgacgggg ttacgccgaa catgatcgac tatttcggac ggccgtatga aggcatcgcc     360
gtgttcgacg gcaaaaagat cactgtaaca gggacccctgt ggaacggcaa caaaattatc     420
gacgagcgcc tgatcaaccc cgacggctcc ctgctgttcc gagtaaccat caacggagtg     480
accggctggc ggctgtgcga acgcattctg gcgtaa                               516
```

<210> SEQ ID NO 26
<211> LENGTH: 300
<212> TYPE: DNA
<213> ORGANISM: Artificial
<220> FEATURE:
<223> OTHER INFORMATION: DNA sequence of the synthetic 3' UTR, T-Zm.
      GST43.nno:1.

<400> SEQUENCE: 26

```
tccagggcgc ctgcttgttt gctgccaaga gagtgttttg tgtactgctg ctgccgagaa      60
atatatattt ttttctttca ccacctcgtg tgcagcagtt gttttttgtt tggatggata     120
aatgtttcta gtactgtgga ggctgcatct gcatctgttt gtaaatggat gaaatatgaa     180
taaaaagttt tgtttctcat accccatgtg tcttgtgttt gcatgcacgc cgtgctagtt     240
tggttttggg tttctagaga aaacattttg tttgcttgtt tctctatagg atgtgaagaa     300
```

PLANT REGULATORY ELEMENTS AND USES THEREOF

REFERENCE TO RELATED APPLICATION

This application is a continuation of U.S. application Ser. No. 16/530,593, filed Aug. 2, 2019 (pending), which application claims the benefit of priority to U.S. provisional application No. 62/714,228, filed Aug. 3, 2018, which are herein incorporated by reference in their entireties.

INCORPORATION OF SEQUENCE LISTING

The sequence listing that is contained in the file named "38-21-62691-0001_Seqlist_ST25.txt", is 31,060 bytes (as measured in Microsoft Windows®), was created on Jul. 2, 2019, and is filed herewith by electronic submission and incorporated by reference herein.

FIELD OF THE INVENTION

The invention relates to the field of plant molecular biology and plant genetic engineering. More specifically, the invention relates to DNA molecules useful for modulating gene expression in plants.

BACKGROUND

Regulatory elements are genetic elements that regulate gene activity by modulating the transcription of an operably linked transcribable DNA molecule. Such elements may include promoters, leaders, introns, and 3' untranslated regions and are useful in the field of plant molecular biology and plant genetic engineering.

SUMMARY OF THE INVENTION

The invention provides novel synthetic gene regulatory elements for use in plants. The invention also provides recombinant DNA molecules constructs comprising the regulatory elements. The present invention also provides transgenic plant cells, plants, and seeds comprising the regulatory elements. In one embodiment, the regulatory elements are operably linked to a transcribable DNA molecule. In certain embodiments, the transcribable DNA molecule may be heterologous with respect to the regulatory sequence. Thus, a regulatory element sequence provided by the invention may, in particular embodiments, be defined as operably linked to a heterologous transcribable DNA molecule. The present invention also provides methods of using the regulatory elements and making and using the recombinant DNA molecules comprising the regulatory elements, and the transgenic plant cells, plants, and seeds comprising the regulatory elements operably linked to a transcribable DNA molecule.

Thus, in one aspect, the invention provides a recombinant DNA molecule comprising a DNA sequence selected from the group consisting of: (a) a sequence with at least about 85 percent sequence identity to any of SEQ ID NOs:1-19 and SEQ ID NO:26; (b) a sequence comprising any of SEQ ID NOs:1-19 and SEQ ID NO:26; and (c) a fragment of any of SEQ ID NOs:1-19 and SEQ ID NO:26, wherein the fragment has gene-regulatory activity; wherein the sequence is operably linked to a heterologous transcribable DNA molecule. By "heterologous transcribable DNA molecule." it is meant that the transcribable DNA molecule is heterologous with respect to the polynucleotide sequence to which it is operably linked. In specific embodiments, the recombinant DNA molecule comprises a DNA sequence having at least about 85 percent, at least about 86 percent, at least about 87 percent, at least about 88 percent, at least about 89 percent, at least about 90 percent, at least 91 percent, at least 92 percent, at least 93 percent, at least 94 percent, at least 95 percent, at least 96 percent, at least 97 percent, at least 98 percent, or at least 99 percent sequence identity to the DNA sequence of any of SEQ ID NOs:1-19 and SEQ ID NO:26. In particular embodiments, the DNA sequence comprises a regulatory element. In some embodiments, the regulatory element comprises a promoter. In still other embodiments, the regulatory element comprises an intron. In still other embodiments, the regulatory element comprises a 3' UTR. In still other embodiments, the heterologous transcribable DNA molecule comprises a gene of agronomic interest, such as a gene capable of providing herbicide resistance in plants, or a gene capable of providing plant pest resistance in plants. In still other embodiments, the heterologous transcribable DNA molecule comprises a sequence encoding a small RNA, such as a dsRNA, an miRNA, or siRNA. In still other embodiments, the invention provides a construct comprising a recombinant DNA molecule as provided herein.

In another aspect, provided herein are transgenic plant cells comprising a recombinant DNA molecule comprising a DNA sequence selected from the group consisting of: (a) a sequence with at least about 85 percent sequence identity to any of SEQ ID NOs:1-19 and SEQ ID NO:26; (b) a sequence comprising any of SEQ ID NOs:1-19 and SEQ ID NO:26; and (c) a fragment of any of SEQ ID NOs:1-19 and SEQ ID NO:26, wherein the fragment has gene-regulatory activity; wherein the DNA sequence is operably linked to a heterologous transcribable DNA molecule. In certain embodiments, the transgenic plant cell is a monocotylcdonous plant cell. In other embodiments, the transgenic plant cell is a dicotyledonous plant cell.

In still yet another aspect, further provided herein is a transgenic plant, or part thereof, comprising a recombinant DNA molecule comprising a DNA sequence selected from the group consisting of: a) a sequence with at least 85 percent sequence identity to any of SEQ ID NOs.1-19 and SEQ ID NO:26; b) a sequence comprising any of SEQ ID NOs:1-19 and SEQ ID NO:26; and c) a fragment of any of SEQ ID NOs:1-19 and SEQ ID NO:26, wherein the fragment has gene-regulatory activity; wherein the sequence is operably linked to a heterologous transcribable DNA molecule. In specific embodiments, the transgenic plant is a progeny plant of any generation that comprises the recombinant DNA molecule. A transgenic seed comprising the recombinant DNA molecule that produces such a transgenic plant when grown is also provided herein.

In another aspect, the invention provides a method of producing a commodity product comprising obtaining a transgenic plant or part thereof containing a recombinant DNA molecule of the invention and producing the commodity product therefrom. In one embodiment, the commodity product is seeds, processed seeds, protein concentrate, protein isolate, starch, grains, plant parts, seed oil, biomass, flour and meal.

In still yet another aspect, the invention provides a method of producing a transgenic plant comprising a recombinant DNA molecule of the invention comprising transforming a plant cell with the recombinant DNA molecule of the invention to produce a transformed plant cell and regenerating a transgenic plant from the transformed plant cell.

BRIEF DESCRIPTION OF THE SEQUENCES

SEQ ID NO:1 is a DNA sequence of a synthetic regulatory expression element group (EXP), EXP-Zm.GSP850 comprising a synthetic promoter (P-Zm.GSP850.nno:4), operably linked 5' to a synthetic leader (L-Zm.GSP850.nno: 3).

SEQ ID NO:2 is a DNA sequence of a synthetic promoter. P-Zm.GSP850.nno:4.

SEQ ID NO:3 is a DNA sequence of a synthetic leader. L-Zm.GSP850.nno:3.

SEQ ID NO:4 is a DNA sequence of a synthetic EXP, EXP-Zm.GSP850.nno+Zm.GSI153.nno:2 comprising a synthetic promoter (P-Zm.GSP850.nno:4), operably linked 5' to a synthetic leader (L-Zm.GSP850.nno:3), operably linked 5' to a synthetic intron (I-Zm.GSI153.nno:1).

SEQ ID NO:5 is a DNA sequence of a synthetic intron, I-Zm.GSI153.nno:1.

SEQ ID NO:6 is a DNA sequence of a synthetic EXP, EXP-Zm.GSP990 comprising a synthetic promoter (P-Zm.GSP990.nno:2), operably linked 5' to a synthetic leader (L-Zm.GSP990.nno: 1).

SEQ ID NO:7 is a DNA sequence of a synthetic promoter, P-Zm.GSP990.nno:2.

SEQ ID NO:8 is a DNA sequence of a synthetic leader. L-Zm.GSP990.nno: 1.

SEQ ID NO:9 is a DNA sequence of a synthetic EXP, EXP-Zm.GSP990.nno+Zm.GSI197.nno:2 comprising a synthetic promoter (P-Zm.GSP990.nno:2), operably linked 5' to a synthetic leader (L-Zm.GSP990.nno:1), operably linked 5' to a synthetic intron (I-Zm.GSI197.nno:1).

SEQ ID NO: 10 is a DNA sequence of a synthetic intron, I-Zm.GSI197.nno: 1.

SEQ ID NO: 11 is a DNA sequence of a synthetic EXP, EXP-Zm.GSP850.nno+Zm.GSI140.nno:1 comprising a synthetic promoter (P-Zm.GSP850.nno:4), operably linked 5' to a synthetic leader (L-Zm.GSP850.nno:3), operably linked 5' to a synthetic intron (I-Zm.GSI140.nno:1).

SEQ ID NO: 12 is a DNA sequence of a synthetic intron, I-Zm.GSI140.nno: 1.

SEQ ID NO: 13 is a DNA sequence of a synthetic V UTR, T-Zm.GST9.nno:2.

SEQ ID NO: 14 is a DNA sequence of a synthetic 3' UTR, T-Zm.GST18.nno:2.

SEQ ID NO: 15 is a DNA sequence of a synthetic EXP, EXP-Zm.GSP850.nno+Zm.DnaK:1 comprising a synthetic promoter (P-Zm.GSP850.nno:4), operably linked 5' to a synthetic leader (L-Zm.GSP850.nno:3), operably linked 5' to an intron (I-Zm.DnaK:1).

SEQ ID NO: 16 is DNA sequence of a synthetic EXP, EXP-Zm.GSP990.nno+Zm.DnaK:1 comprising a synthetic promoter (P-Zm.GSP990.nno:2), operably linked 5' to a synthetic leader (L-Zm.GSP990.nno:1), operably linked 5' to an intron (I-Zm.DnaK:1).

SEQ ID NO: 17 is a DNA sequence of a synthetic enhancer, E-Zm.GSP850 which is derived from the synthetic promoter, P-Zm.GSP850.nno:4.

SEQ ID NO: 18 is a DNA sequence of a synthetic enhancer, E-Zm.GSP990 which is derived from the synthetic promoter, P-Zm.GSP990.nno:2.

SEQ ID NO: 19 is a DNA sequence of a 3' UTR, T-Sb.Nltp4-1:1:2 derived from the NLTP4 (non-specific lipid-transfer protein 4) gene from *Sorghum bicolor.*

SEQ ID NO:20 is a synthetic coding sequence optimized for plant expression for β-glucuronidase (GUS) with a processable intron derived from the potato light-inducible tissue-specific ST-LS1 gene (Genbank Accession: X04753).

SEQ ID NO:21 is a DNA sequence of the EXP, EXP-CaMV.35S comprising the 35S promoter and leader derived from the Cauliflower mosaic virus.

SEQ ID NO:22 is a DNA sequence of the intron, I-Zm.D-naK:1 derived from the heat shock protein 70 (Hsp70) gene (DnaK) from *Zea mays.*

SEQ ID NO:23 is a DNA sequence of the 3' UTR, T-Os.LTP:1 derived from the Lipid Transfer Protein-like gene (LTP) from *Oryza sativa.*

SEQ ID NO:24 is a coding sequence for β-glucuronidase (GUS) with a processable intron derived from the potato light-inducible tissue-specific ST-LS1 gene (Genbank Accession: X04753).

SEQ ID NO:25 is a coding sequence for the NanoLuc® luciferase fluorescent protein (Promega, Madison, Wis. 53711), Nluc which was engineered by directed evolution from a deep-sea shrimp (*Oplophorus gacilirostris*) luciferase.

SEQ ID NO:26 is a DNA sequence of a synthetic 3' UTR, T-Zm.GST43.nno:1.

DETAILED DESCRIPTION OF THE INVENTION

The invention provides synthetic regulatory elements having gene-regulatory activity in plants. The nucleotide sequences of these synthetic regulatory elements are provided as SEQ ID NOs:1-18 and SEQ ID NO:26. These synthetic regulatory elements are capable of affecting the expression of an operably linked transcribable DNA molecule in plant tissues, and therefore regulating gene expression of an operably linked transgene in transgenic plants. The invention also provides novel endogenous regulatory elements having gene-regulatory activity in plants and provided as SEQ ID NO: 19. The invention also provides methods of modifying, producing, and using recombinant DNA molecules which contain the provided synthetic and endogenous regulatory elements. The invention also provides compositions that include transgenic plant cells, plants, plant parts, and seeds containing the recombinant DNA molecules of the invention, and methods for preparing and using the same.

The following definitions and methods are provided to better define the present invention and to guide those of ordinary skill in the art in the practice of the present invention. Unless otherwise noted, terms are to be understood according to conventional usage by those of ordinary skill in the relevant art.

DNA Molecules

As used herein, the term "DNA" or "DNA molecule" refers to a double-stranded DNA molecule of genomic or synthetic origin, i.e., a polymer of deoxyribonucleotide bases or a DNA molecule, read from the 5' (upstream) end to the 3' (downstream) end. As used herein, the term "DNA sequence" refers to the nucleotide sequence of a DNA molecule. The nomenclature used herein corresponds to that of Title 37 of the United States Code of Federal Regulations § 1.822, and set forth in the tables in WIPO Standard ST.25 (1998), Appendix 2, Tables 1 and 3.

As used herein, a "recombinant DNA molecule" is a DNA molecule comprising a combination of DNA molecules that would not naturally occur together without human intervention. For instance, a recombinant DNA molecule may be a DNA molecule that is comprised of at least two DNA molecules heterologous with respect to each other, a DNA molecule that comprises a DNA sequence that deviates from DNA sequences that exist in nature, a DNA molecule that comprises a synthetic DNA sequence or a DNA molecule that has been incorporated into a host cell's DNA by genetic transformation or gene editing.

As used herein, a "synthetic nucleotide sequence" or "artificial nucleotide sequence" is a nucleotide sequence that is not known to occur in nature or that is not naturally occurring. The gene-regulatory elements of the present invention comprise synthetic nucleotide sequences. Preferably, synthetic nucleotide sequences share little or no extended homology to natural sequences. Extended homology in this context generally refers to 100% sequence identity extending beyond about 25 nucleotides of contiguous sequence.

Reference in this application to an "isolated DNA molecule", or an equivalent term or phrase, is intended to mean that the DNA molecule is one that is present alone or in combination with other compositions, but not within its natural environment. For example, nucleic acid elements such as a coding sequence, intron sequence, untranslated leader sequence, promoter sequence, transcriptional termination sequence, and the like, that are naturally found within the DNA of the genome of an organism are not considered to be "isolated" so long as the element is within the genome of the organism and at the location within the genome in which it is naturally found. However, each of these elements, and subparts of these elements, would be "isolated" within the scope of this disclosure so long as the element is not within the genome of the organism and at the location within the genome in which it is naturally found. Similarly, a nucleotide sequence encoding an insecticidal protein or any naturally occurring insecticidal variant of that protein would be an isolated nucleotide sequence so long as the nucleotide sequence was not within the DNA of the bacterium from which the sequence encoding the protein is naturally found. A synthetic nucleotide sequence encoding the amino acid sequence of the naturally occurring insecticidal protein would be considered to be isolated for the purposes of this disclosure. For the purposes of this disclosure, any transgenic nucleotide sequence, i.e., the nucleotide sequence of the DNA inserted into the genome of the cells of a plant or bacterium, or present in an extrachromosomal vector, would be considered to be an isolated nucleotide sequence whether it is present within the plasmid or similar structure used to transform the cells, within the genome of the plant or bacterium, or present in detectable amounts in tissues, progeny, biological samples or commodity products derived from the plant or bacterium.

As used herein, the term "sequence identity" refers to the extent to which two optimally aligned polynucleotide sequences or two optimally aligned polypeptide sequences are identical. An optimal sequence alignment is created by manually aligning two sequences, e.g., a reference sequence and another sequence, to maximize the number of nucleotide matches in the sequence alignment with appropriate internal nucleotide insertions, deletions, or gaps. As used herein, the term "reference sequence" refers to a DNA sequence provided as SEQ ID NOs:1-19 and SEQ ID NO:26.

As used herein, the term "percent sequence identity" or "percent identity" or "% identity" is the identity fraction multiplied by 100. The "identity fraction" for a sequence optimally aligned with a reference sequence is the number of nucleotide matches in the optimal alignment, divided by the total number of nucleotides in the reference sequence, e.g., the total number of nucleotides in the full length of the entire reference sequence. Thus, one embodiment of the invention provides a DNA molecule comprising a sequence that, when optimally aligned to a reference sequence, provided herein as SEQ ID NOs:1-19 and SEQ ID NO:26, has at least about 85 percent identity, at least about 86 percent identity, at least about 87 percent identity, at least about 88 percent identity, at least about 89 percent identity, at least about 90 percent identity, at least about 91 percent identity, at least about 92 percent identity, at least about 93 percent identity, at least about 94 percent identity, at least about 95 percent identity, at least about 96 percent identity, at least about 97 percent identity, at least about 98 percent identity, at least about 99 percent identity, or at least about 100 percent identity to the reference sequence. DNA molecules having a percent sequence identity with reference molecule may exhibit the activity of the reference sequence.

Regulatory Elements

Regulatory elements such as promoters, leaders (also known as 5' UTRs), enhancers, introns, and transcription termination regions (or 3' UTRs) play an integral part in the overall expression of genes in living cells. The term "regulatory element," as used herein, refers to a DNA molecule having gene-regulatory activity. The term "gene-regulatory activity," as used herein, refers to the ability to affect the expression of an operably linked transcribable DNA molecule, for instance by affecting the transcription and/or translation of the operably linked transcribable DNA molecule. Regulatory elements, such as promoters, leaders, enhancers, introns and 3' UTRs that function in plants are useful for modifying plant phenotypes through genetic engineering.

As used herein, a "regulatory expression element group" or "EXP" sequence may refer to a group of operably linked regulatory elements, such as enhancers, promoters, leaders, and introns. For example, a regulatory expression element group may be comprised, for instance, of a promoter operably linked 5' to a leader sequence. EXP's useful in practicing the present invention include SEQ ID NOs:1, 4, 6, 9, 11, 15, and 16.

Regulatory elements may be characterized by their gene expression pattern, e.g., positive and/or negative effects such as constitutive expression or temporal, spatial, developmental, tissue, environmental, physiological, pathological, cell cycle, and/or chemically responsive expression, and any combination thereof, as well as by quantitative or qualitative indications. As used herein, a "gene expression pattern" is any pattern of transcription of an operably linked DNA molecule into a transcribed RNA molecule. The transcribed RNA molecule may be translated to produce a protein molecule or may provide an antisense or other regulatory RNA molecule, such as a double-stranded RNA (dsRNA), a transfer RNA (tRNA), a ribosomal RNA (rRNA), a microRNA (miRNA), a small interfering RNA (siRNA), and the like.

As used herein, the term "protein expression" is any pattern of translation of a transcribed RNA molecule into a protein molecule. Protein expression may be characterized by its temporal, spatial, developmental, or morphological qualities, as well as by quantitative or qualitative indications.

A promoter is useful as a regulatory element for modulating the expression of an operably linked transcribable DNA molecule. As used herein, the term "promoter" refers generally to a DNA molecule that is involved in recognition and binding of RNA polymerase II and other proteins, such as trans-acting transcription factors, to initiate transcription. A promoter may be initially isolated from the 5' untranslated region (5' UTR) of a genomic copy of a gene. Alternately, promoters may be synthetically produced or manipulated DNA molecules. Promoters may also be chimeric. Chimeric promoters are produced through the fusion of two or more heterologous DNA molecules. Promoters useful in practicing the present invention include promoter elements provided as SEQ ID NOs:2 and 7, or comprised within any of SEQ ID NOs: 1, 4, 6, 9, 11, 15, and 16, or fragments or variants thereof. In specific embodiments of the invention, the claimed DNA molecules and any variants or derivatives thereof as described herein, are further defined as comprising promoter activity, i.e., are capable of acting as a promoter in a host cell, such as in a transgenic plant. In still further specific embodiments, a fragment may be defined as exhibiting promoter activity possessed by the starting promoter molecule from which it is derived, or a fragment may comprise a "minimal promoter" which provides a basal level of transcription and is comprised of a TATA box or equivalent DNA sequence for recognition and binding of the RNA polymerase II complex for initiation of transcription.

In one embodiment, fragments of an EXP sequence or a promoter sequence disclosed herein are provided. Promoter fragments may comprise promoter activity, as described above, and may be useful alone or in combination with other promoters and promoter fragments, such as in constructing chimeric promoters, or in combination with other expression elements and expression element fragments. In specific embodiments, fragments of a promoter are provided comprising at least about 50, at least about 75, at least about 95, at least about 100, at least about 125, at least about 150, at least about 175, at least about 200, at least about 225, at least about 250, at least about 275, at least about 300, at least about 500, at least about 600, at least about 700, at least about 750, at least about 800, at least about 900, or at least about 1000 contiguous nucleotides, or longer, of a DNA molecule having promoter activity as disclosed herein.

Methods for producing such fragments from a starting promoter molecule are well known in the art.

In further embodiments, fragments of enhancer or intron sequences disclosed herein are provided. Enhancer or intron fragments may comprise the activity of the base molecule from which they were derived, and may be useful alone or in combination with other regulatory elements including promoters, leaders, other enhancers, other introns, or fragments thereof. In specific embodiments, fragments of an enhancer or intron are provided comprising at least about 50, at least about 75, at least about 95, at least about 100, at least about 125, at least about 150, at least about 175, at least about 200, at least about 225, at least about 250, at least about 275, at least about 300, at least about 500, at least about 600, at least about 700, at least about 750, at least about 800, at least about 900, or at least about 1000 contiguous nucleotides, or longer, of a DNA molecule having enhancer or intron activity as disclosed herein. Methods for producing such fragments from a starting molecule are well known in the art.

In other embodiments, fragments of 3' UTR sequences disclosed herein are provided. 3' UTR fragments may comprise the activity of the base 3' UTR molecule from which they were derived, and may be useful alone or in combination with other regulatory elements including promoters, leaders, introns, or fragments thereof. In specific embodiments, fragments of an intron are provided comprising at least about 50, at least about 75, at least about 95, at least about 100, at least about 125, at least about 150, at least about 175, at least about 200, at least about 225, at least about 250, at least about 275, at least about 300, at least about 500, at least about 600, at least about 700, at least about 750, at least about 800, at least about 900, or at least about 1000 contiguous nucleotides, or longer, of a DNA molecule having 3' UTR activity as disclosed herein. Methods for producing such fragments from a starting 3' UTR molecule are well known in the art.

Compositions derived from any of the promoter elements provided as SEQ ID NOs:2 and 7, or comprised within any of SEQ ID NOs:1, 4, 6, 9, 11, 15, and 16 such as internal or 5' deletions, for example, can be produced using methods known in the art to improve or alter expression, including by removing elements that have either positive or negative effects on expression; duplicating elements that have positive or negative effects on expression; and/or duplicating or removing elements that have tissue- or cell-specific effects on expression.

Compositions derived from any of the promoter elements provided as SEQ ID NOs:2 and 7, or comprised within any of SEQ ID NOs:1, 4, 6, 9, 11, 15, and 16, comprised of 3' deletions in which the TATA box element or equivalent sequence thereof and downstream sequence is removed can be used, for example, to make enhancer elements. Further deletions can be made to remove any elements that have positive or negative; tissue-specific; cell-specific; or timing-specific (such as, but not limited to, circadian rhythm) effects on expression. Any of the promoter elements provided as SEQ ID NOs:2 and 7, or comprised within any of SEQ ID NOs:1, 4, 6, 9, 11, 15, and 16 and fragments or enhancers derived therefrom can be used to make chimeric transcriptional regulatory element compositions.

In accordance with the invention, a promoter or promoter fragment may be analyzed for the presence of known promoter elements, i.e., DNA sequence characteristics, such as a TATA box and other known transcription factor binding site motifs. Identification of such known promoter elements may be used by one of skill in the art to design variants of the promoter having a similar expression pattern to the original promoter.

As used herein, the term "leader" refers to a DNA molecule isolated from the untranslated 5' region (5' UTR) a gene and defined generally as a nucleotide segment between the transcription start site (TSS) and the protein coding sequence start site. Alternately, leaders may be synthetically produced or manipulated DNA elements. A leader can be used as a 5' regulatory element for modulating expression of an operably linked transcribable DNA molecule. Leader molecules may be used with a heterologous promoter or with their native promoter. Leaders useful in practicing the present invention include SEQ ID NOs:3 and 8; or any of the leader elements comprised within any of SEQ ID NOs:1, 4, 6, 9, 11, 15, and 16 or fragments or variants thereof. In specific embodiments, such DNA sequences may be defined as being capable of acting as a leader in a host cell, including, for example, a transgenic plant cell. In one embodiment, such sequences are decoded as comprising leader activity.

The leader sequences (also referred to as 5' UTRs) presented as SEQ ID NOs:3 and 8 or any of the leader elements comprised within any of SEQ ID NOs:1, 4, 6, 9, 11, 15, and 16 may be comprised of regulatory elements, or may adopt secondary structures that can have an effect on transcription or translation of an operably linked transcribable DNA molecule. The leader sequences presented as SEQ ID NOs:3 and 8 or any of the leader elements comprised within any of SEQ ID NOs:1, 4, 6, 9, 11, 15, and 16 can be used in accordance with the invention to make chimeric regulatory elements that affect transcription or translation of a an operably linked transcribable DNA molecule.

As used herein, the term "intron" refers to a DNA molecule that may be isolated or identified from a gene and may be defined generally as a region spliced out during messenger RNA (mRNA) processing prior to translation. Alternately, an intron may be a synthetically produced or manipulated DNA element. An intron may contain enhancer elements that effect the transcription of operably linked genes. An intron may be used as a regulatory element for modulating expression of an operably linked transcribable DNA molecule. A construct may comprise an intron, and the intron may or may not be heterologous with respect to the transcribable DNA molecule. Examples of introns in the art include the rice actin intron and the corn HSP70 intron.

In plants, the inclusion of some introns in gene constructs leads to increased mRNA and protein accumulation relative to constructs lacking the intron. This effect has been termed "intron mediated enhancement" (IME) of gene expression. Introns known to stimulate expression in plants have been identified in maize genes (e.g., tubA1, Adh1, Sh1, and Ubi1), in rice genes (e.g., tpi) and in dicotyledonous plant genes like those from *petunia* (e.g., rbcS), potato (e.g., st-ls1) and from *Arabidopsis thaliana* (e.g., ubq3 and pat1). It has been shown that deletions or mutations within the splice sites of an intron reduce gene expression, indicating that splicing might be needed for IME. However, IME in dicotyledonous plants has been shown by point mutations within the splice sites of the pat1 gene from *A. thaliana*. Multiple uses of the same intron in one plant has been shown to exhibit disadvantages. In those cases, it is necessary to have a collection of basic control elements for the construction of appropriate recombinant DNA elements. Exemplary introns useful in practicing the present invention are presented as SEQ ID NOs:5, 10, and 12.

As used herein, the terms "3' transcription termination molecule," "3' untranslated region" or "3' UTR" refer to a DNA molecule that is used during transcription to the untranslated region of the 3' portion of an mRNA molecule. The 3' untranslated region of an mRNA molecule may be generated by specific cleavage and 3' polyadenylation, also known as a poly A tail. A 3' UTR may be operably linked to and located downstream of a transcribable DNA molecule and may include a polyadenylation signal and other regulatory signals capable of affecting transcription, mRNA processing, or gene expression. PolyA tails are thought to function in mRNA stability and in initiation of translation. Examples of 3' transcription termination molecules in the art are the nopaline synthase 3' region, wheat hsp17 3' region, pea rubisco small subunit 3' region, cotton E6 3' region, and the coixin 3' UTR.

3' UTRs typically find beneficial use for the recombinant expression of specific DNA molecules. A weak 3' UTR has the potential to generate read-through, which may affect the expression of the DNA molecule located in the neighboring expression cassettes. Appropriate control of transcription termination can prevent read-through into DNA sequences (e.g., other expression cassettes) localized downstream and can further allow efficient recycling of RNA polymerase to improve gene expression. Efficient termination of transcription (release of RNA Polymerase II from the DNA) is prerequisite for re-initiation of transcription and thereby directly affects the overall transcript level. Subsequent to transcription termination, the mature mRNA is released from the site of synthesis and template transported to the cytoplasm. Eukaryotic mRNAs are accumulated as poly(A) forms in vivo, making it difficult to detect transcriptional termination sites by conventional methods. However, prediction of functional and efficient 3' UTRs by bioinformatics methods is difficult in that there are no conserved DNA sequences that would allow easy prediction of an effective 3' UTR.

From a practical standpoint, it is typically beneficial that a 3' UTR used in an expression cassette possesses the following characteristics. First, the 3' UTR should be able to efficiently and effectively terminate transcription of the transgene and prevent read-through of the transcript into any neighboring DNA sequence, which can be comprised of another expression cassette as in the case of multiple expression cassettes residing in one transfer DNA (T-DNA), or the neighboring chromosomal DNA into which the T-DNA has inserted. Second, the 3' UTR should not cause a reduction in the transcriptional activity imparted by the promoter, leader, enhancers, and introns that are used to drive expression of the DNA molecule. Finally, in plant biotechnology, the 3' UTR is often used for priming of amplification reactions of reverse transcribed RNA extracted from the transformed plant and used to: (1) assess the transcriptional activity or expression of the expression cassette once integrated into the plant chromosome; (2) assess the copy number of insertions within the plant DNA; and (3) assess zygosity of the resulting seed after breeding. The 3' UTR is also used in amplification reactions of DNA extracted from the transformed plant to characterize the intactness of the inserted cassette. 3' UTRs useful in practicing the present invention are presented as SEQ ID NOs:13, 14, 19, and 26.

As used herein, the term "enhancer" or "enhancer element" refers to a cis-acting regulatory element, a.k.a. cis-element, which confers an aspect of the overall expression pattern, but is usually insufficient alone to drive transcription, of an operably linked transcribable DNA molecule. Unlike promoters, enhancer elements do not usually include a transcription start site (TSS) or TATA box or equivalent DNA sequence. A promoter or promoter fragment may naturally comprise one or more enhancer elements that affect the transcription of an operably linked DNA sequence. An enhancer element may also be fused to a promoter to produce a chimeric promoter cis-element, which confers an aspect of the overall modulation of gene expression.

Many promoter enhancer elements are believed to bind DNA-binding proteins and/or affect DNA topology, producing local conformations that selectively allow or restrict access of RNA polymerase to the DNA template or that facilitate selective opening of the double helix at the site of transcriptional initiation. An enhancer element may function to bind transcription factors that regulate transcription. Some enhancer elements bind more than one transcription factor, and transcription factors may interact with different affinities with more than one enhancer domain. Enhancer elements can be identified by a number of techniques, including deletion analysis, i.e., deleting one or more nucleotides from the 5' end or internal to a promoter; DNA binding protein analysis using DNase I footprinting, methylation interference, electrophoresis mobility-shift assays, in vivo genomic footprinting by ligation-mediated polymerase chain reaction (PCR), and other conventional assays or by DNA sequence similarity analysis using known m-element motifs or enhancer elements as a target sequence or target motif with conventional DNA sequence comparison methods, such as BLAST. The fine structure of an enhancer domain can be further studied by mutagenesis (or substitution) of one or more nucleotides or by other conventional methods known in the art. Enhancer elements can be obtained by chemical synthesis or by isolation from regulatory elements that include such elements, and they can be synthesized with additional flanking nucleotides that contain useful restriction enzyme sites to facilitate subsequence manipulation. Thus, the design, construction, and use of enhancer elements according to the methods disclosed herein for modulating the expression of operably linked transcribable DNA molecules are encompassed by the invention. Exemplary enhancers useful in practicing this invention are presented as SEQ ID NOs:17 and 18.

As used herein, the term "chimeric" refers to a single DNA molecule produced by fusing a first DNA molecule to a second DNA molecule, where neither the first nor the second DNA molecule would normally be found in that configuration, i.e. fused to the other. The chimeric DNA molecule is thus a new DNA molecule not otherwise normally found in nature. As used herein, the term "chimeric promoted" refers to a promoter produced through such manipulation of DNA molecules. A chimeric promoter may combine two or more DNA fragments for example, the fusion of a promoter to an enhancer element. Thus, the design, construction, and use of chimeric promoters according to the methods disclosed herein for modulating the expression of operably linked transcribable DNA molecules are encompassed by the present invention.

Chimeric regulatory elements can be designed to comprise various constituent elements which may be operatively linked by various methods known in the art, such as restriction enzyme digestion and ligation, ligation independent cloning, modular assembly of PCR products during amplification, or direct chemical synthesis of the regulatory element, as well as other methods known in the art. The resulting various chimeric regulatory elements can be comprised of the same, or variants of the same, constituent elements but differ in the DNA sequence or DNA sequences that comprise the linking DNA sequence or sequences that allow the constituent parts to be operatively linked. In the invention, the DNA sequences provided as SEQ ID NOs:1-19 and SEQ ID NO:26 may provide regulatory element reference sequences, wherein the constituent elements that comprise the reference sequence may be joined by methods known in the art and may comprise substitutions, deletions, and/or insertions of one or more nucleotides or mutations that naturally occur in bacterial and plant cell transformation.

As used herein, the term "variant" refers to a second DNA molecule, such as a regulatory element, that is in composition similar, but not identical to, a first DNA molecule, and wherein the second DNA molecule still maintains the general functionality, i.e. the same or similar expression pattern, for instance through more or less equivalent transcriptional activity, of the first DNA molecule. A variant may be a shorter or truncated version of the first DNA molecule or an altered version of the sequence of the first DNA molecule, such as one with different restriction enzyme sites and/or internal deletions, substitutions, or insertions. A "variant" can also encompass a regulatory element having a nucleotide sequence comprising a substitution, deletion, or insertion of one or more nucleotides of a reference sequence, wherein the derivative regulatory element has more or less or equivalent transcriptional or translational activity than the corresponding parent regulatory molecule. Regulatory element "variants" will also encompass variants arising from mutations that naturally occur in bacterial and plant cell transformation. In the present invention, a polynucleotide sequence provided as SEQ ID NOs:1-19 and SEQ ID NO:26 may be used to create variants that are similar in composition, but not identical to, the DNA sequence of the original regulatory element, while still maintaining the general functionality, i.e., the same or similar expression pattern, of the original regulatory element. Production of such variants of the invention is well within the ordinary skill of the art in light of the disclosure and is encompassed within the scope of the invention.

The efficacy of the modifications, duplications, or deletions described herein on the desired expression aspects of a particular transgene may be tested empirically in stable and transient plant assays, such as those described in the working examples herein, so as to validate the results, which may vary depending upon the changes made and the goal of the change in the starting DNA molecule.

Constructs

As used herein, the term "construct" means any recombinant DNA molecule such as a plasmid, cosmid, virus, phage, or linear or circular DNA or RNA molecule, derived from any source, capable of genomic integration or autonomous replication, comprising a DNA molecule where at least one DNA molecule has been linked to another DNA molecule in a functionally operative manner, i.e. operably linked. As used herein, the term "vector" means any construct that may be used for the purpose of transformation, i.e., the introduction of heterologous DNA or RNA into a host cell. A construct typically includes one or more expression cassettes. As used herein, an "expression cassette" refers to a DNA molecule comprising at least a transcribable DNA molecule operably linked to one or more regulatory elements, typically at least a promoter and a 3' UTR.

As used herein, the term "operably linked" refers to a first DNA molecule joined to a second DNA molecule, wherein the first and second DNA molecules are so arranged that the first DNA molecule affects the function of the second DNA molecule. The two DNA molecules may or may not be part of a single contiguous DNA molecule and may or may not be adjacent. For example, a promoter is operably linked to a transcribable DNA molecule if the promoter modulates transcription of the transcribable DNA molecule of interest in a cell. A leader, for example, is operably linked to DNA sequence when it is capable of affecting the transcription or translation of the DNA sequence.

The constructs of the invention may be provided, in one embodiment, as double tumor-inducing (Ti) plasmid border constructs that have the right border (RB or AGRtu.RB) and left border (LB or AGRtu.LB) regions of the Ti plasmid isolated from *Agrobacterium tumefaciens* comprising a T-DNA that, along with transfer molecules provided by the *A. tumefaciens* cells, permit the integration of the T-DNA into the genome of a plant cell (see, e.g., U.S. Pat. No. 6,603,061). The constructs may also contain the plasmid backbone DNA segments that provide replication function and antibiotic selection in bacterial cells, e.g., an *Escherichia coli* origin of replication such as ori322, a broad host range origin of replication such as oriV or oriRi, and a coding region for a selectable marker such as Spec/Strp that encodes for Tn7 aminoglycoside adenyltransferase (aadA) conferring resistance to spectinomycin or streptomycin, or a gentamicin (Gm, Gent) selectable marker gene. For plant transformation, the host bacterial strain is often *A. tumefaciens* ABI, C58, or LBA4404, however other strains known to those skilled in the art of plant transformation can function in the invention.

Methods are known in the art for assembling and introducing constructs into a cell in such a manner that the transcribable DNA molecule is transcribed into a functional mRNA molecule that is translated and expressed as a protein. For the practice of the invention, conventional compositions and methods for preparing and using constructs and host cells are well known to one skilled in the art. Typical vectors useful for expression of nucleic acids in higher plants are well known in the art and include vectors derived from the Ti plasmid of *Agrobacterium tumefaciens* and the pCaMVCN transfer control vector.

Various regulatory elements may be included in a construct, including any of those provided herein. Any such regulatory elements may be provided in combination with other regulatory elements. Such combinations can be designed or modified to produce desirable regulatory features. In one embodiment, constructs of the invention comprise at least one regulatory element operably linked to a transcribable DNA molecule operably linked to a 3' UTR.

Constructs of the invention may include any promoter or leader provided herein or known in the art. For example, a promoter of the invention may be operably linked to a heterologous non-translated 5' leader such as one derived from a heat shock protein gene. Alternatively, a leader of the invention may be operably linked to a heterologous promoter such as the Cauliflower Mosaic Virus 35S transcript promoter.

Expression cassettes may also include a transit peptide coding sequence that encodes a peptide that is useful for sub-cellular targeting of an operably linked protein, particularly to a chloroplast, leucoplast, or other plastid organelle; mitochondria; peroxisome; vacuole; or an extracellular location. Many chloroplast-localized proteins are expressed from nuclear genes as precursors and are targeted to the chloroplast by a chloroplast transit peptide (CTP). Examples of such isolated chloroplast proteins include, but are not limited to, those associated with the small subunit (SSU) of ribulose-1,5-bisphosphate carboxylase, ferredoxin, ferredoxin oxidoreductase, the light-harvesting complex protein I and protein II, thioredoxin F, and enolpyruvyl shikimate phosphate synthase (EPSPS). Chloroplast transit peptides are described, for example, in U.S. Pat. No. 7,193,133. It has been demonstrated that non-chloroplast proteins may be targeted to the chloroplast by the expression of a heterologous CTP operably linked to the transgene encoding a non-chloroplast proteins.

Transcribable DNA Molecules

As used herein, the term "transcribable DNA molecule" refers to any DNA molecule capable of being transcribed into an RNA molecule, including, but not limited to, those having protein coding sequences and those producing RNA molecules having sequences useful for gene suppression. The type of DNA molecule can include, but is not limited to, a DNA molecule from the same plant, a DNA molecule from another plant, a DNA molecule from a different organism, or a synthetic DNA molecule, such as a DNA molecule containing an antisense message of a gene, or a DNA molecule encoding an artificial, synthetic, or otherwise modified version of a transgene. Exemplary transcribable DNA molecules for incorporation into constructs of the invention include, e.g., DNA molecules or genes from a species other than the species into which the DNA molecule is incorporated or genes that originate from, or are present in, the same species, but are incorporated into recipient cells by genetic engineering methods rather than classical breeding techniques.

A "transgene" refers to a transcribable DNA molecule heterologous to a host cell at least with respect to its location in the host cell genome and/or a transcribable DNA molecule artificially incorporated into a host cell's genome in the current or any prior generation of the cell.

A regulatory element, such as a promoter of the invention, may be operably linked to a transcribable DNA molecule that is heterologous with respect to the regulatory element. As used herein, the term "heterologous" refers to the combination of two or more DNA molecules when such a combination is not normally found in nature. For example, the two DNA molecules may be derived from different species and/or the two DNA molecules may be derived from different genes, e.g., different genes from the same species or the same genes from different species. A regulatory element is thus heterologous with respect to an operably linked transcribable DNA molecule if such a combination is not normally found in nature, i.e., the transcribable DNA molecule docs not naturally occur operably linked to the regulatory element.

The transcribable DNA molecule may generally be any DNA molecule for which expression of a transcript is desired. Such expression of a transcript may result in translation of the resulting mRNA molecule, and thus protein expression. Alternatively, for example, a transcribable DNA molecule may be designed to ultimately cause decreased expression of a specific gene or protein. In one embodiment, this may be accomplished by using a transcribable DNA molecule that is oriented in the antisense direction. One of ordinary skill in the art is familiar with using such antisense technology. Any gene may be negatively regulated in this manner, and, in one embodiment, a transcribable DNA molecule may be designed for suppression of a specific gene through expression of a dsRNA, siRNA or miRNA molecule.

Thus, one embodiment of the invention is a recombinant DNA molecule comprising a regulatory element of the invention, such as those provided as SEQ ID NOs:1-19 and SEQ ID NO:26, operably linked to a heterologous transcribable DNA molecule so as to modulate transcription of the transcribable DNA molecule at a desired level or in a desired pattern when the construct is integrated in the genome of a transgenic plant cell. In one embodiment, the transcribable DNA molecule comprises a protein-coding region of a gene and in another embodiment the transcribable DNA molecule comprises an antisense region of a gene.

Genes of Agronomic Interest

A transcribable DNA molecule may be a gene of agronomic interest. As used herein, the term "gene of agronomic interest" refers to a transcribable DNA molecule that, when expressed in a particular plant tissue, cell, or cell type, confers a desirable characteristic. The product of a gene of agronomic interest may act within the plant in order to cause an effect upon the plant morphology, physiology, growth, development, yield, grain composition, nutritional profile, disease or pest resistance, and/or environmental or chemical tolerance or may act as a pesticidal agent in the diet of a pest that feeds on the plant. In one embodiment of the invention, a regulatory element of the invention is incorporated into a construct such that the regulatory element is operably linked to a transcribable DNA molecule that is a gene of agronomic interest.

In a transgenic plant containing such a construct, the expression of the gene of agronomic interest can confer a beneficial agronomic trait. A beneficial agronomic trait may include, for example, but is not limited to, herbicide tolerance, insect control, modified yield, disease resistance, pathogen resistance, modified plant growth and development, modified starch content, modified oil content, modified fatty acid content, modified protein content, modified fruit ripening, enhanced animal and human nutrition, biopolymer productions, environmental stress resistance, pharmaceutical peptides, improved processing qualities, improved flavor, hybrid seed production utility, improved fiber production, and desirable biofuel production.

Non-limiting examples of genes of agronomic interest known in the art include those for herbicide resistance (U.S. Pat. Nos. 6,803,501; 6,448,476; 6,248,876; 6,225,114; 6,107,549; 5,866,775; 5,804,425; 5,633,435; and 5,463, 175), increased yield (U.S. Pat. Nos. USRE38,446; U.S. Pat. Nos. 6,716,474; 6,663,906; 6,476,295; 6,441,277; 6,423,828; 6,399,330; 6,372,211; 6,235,971; 6,222,098; and 5,716,837), insect control (U.S. Pat. Nos. 6,809,078; 6,713,063; 6,686,452; 6,657,046; 6,645,497; 6,642,030; 6,639,054; 6,620,988; 6,593,293; 6,555,655; 6,538,109; 6,537,756; 6,521,442; 6,501,009; 6,468,523; 6,326,351; 6,313,378; 6,284,949; 6,281,016; 6,248,536; 6,242,241; 6,221,649; 6,177,615; 6,156,573; 6,153,814; 6,110,464; 6,093,695; 6,063,756; 6,063,597; 6,023,013; 5,959,091; 5,942,664; 5,942,658, 5,880,275; 5,763,245; and 5,763,241), fungal disease resistance (U.S. Pat. Nos. 6,653,280; 6,573,361; 6,506,962; 6,316,407; 6,215,048; 5,516,671; 5,773,696; 6,121,436; 6,316,407; and 6,506,962), virus resistance (U.S. Pat. Nos. 6,617,496; 6,608,241; 6,015,940; 6,013,864; 5,850,023; and 5,304,730), nematode resistance (U.S. Pat. No. 6,228,992), bacterial disease resistance (U.S. Pat. No. 5,516,671), plant growth and development (U.S. Pat. Nos. 6,723,897 and 6,518,488), starch production (U.S. Pat. Nos. 6,538,181; 6,538,179; 6,538,178; 5,750,876; 6,476,295), modified oils production (U.S. Pat. Nos. 6,444,876; 6,426,447; and 6,380,462), high oil production (U.S. Pat. Nos. 6,495,739; 5,608,149; 6,483,008; and 6,476,295), modified fatty acid content (U.S. Pat. Nos. 6,828,475; 6,822,141; 6,770,465; 6,706,950; 6,660,849; 6,596,538; 6,589,767; 6,537,750; 6,489,461; and 6,459,018), high protein production (U.S. Pat. No. 6,380,466), fruit ripening (U.S. Pat. No. 5,512,466), enhanced animal and human nutrition (U.S. Pat. Nos. 6,723,837; 6,653,530; 6,5412,59; 5,985,605; and 6,171,640), biopolymers (U.S. Pat. Nos. USRE37,543; U.S. Pat. Nos. 6,228,623; and 5,958,745, and 6,946,588), environmental stress resistance (U.S. Pat. No. 6,072,103), pharmaceutical peptides and secretable peptides (U.S. Pat. Nos. 6,812,379; 6,774,283; 6,140,075; and 6,080,560), improved processing traits (U.S. Pat. No. 6,476,295), improved digestibility (U.S. Pat. No. 6,531,648) low raffinose (U.S. Pat. No. 6,166,292), industrial enzyme production (U.S. Pat. No. 5,543,576), improved flavor (U.S. Pat. No. 6,011,199), nitrogen fixation (U.S. Pat. No. 5,229,114), hybrid seed production (U.S. Pat. No. 5,689,041), fiber production (U.S. Pat. Nos. 6,576,818; 6,271,443; 5,981,834; and 5,869,720) and biofuel production (U.S. Pat. No. 5,998,700).

Alternatively, a gene of agronomic interest can affect the above mentioned plant characteristics or phenotypes by encoding a RNA molecule that causes the targeted modulation of gene expression of an endogenous gene, for example by antisense (see, e.g. U.S. Pat. No. 5,107,065); inhibitory RNA ("RNAi," including modulation of gene expression by miRNA-, siRNA-, trans-acting siRNA-, and phased sRNA-mediated mechanisms, e.g., as described in published applications U.S. 2006/0200878 and U.S. 2008/0066206, and in U.S. patent application Ser. No. 11/974,469); or cosuppression-mediated mechanisms. The RNA could also be a catalytic RNA molecule (e.g., a ribozyme or a riboswitch; see, e.g., U.S. 2006/0200878) engineered to cleave a desired endogenous mRNA product. Methods are known in the art for constructing and introducing constructs into a cell in such a manner that the transcribable DNA molecule is transcribed into a molecule that is capable of causing gene suppression.

Selectable Markers

Selectable marker transgenes may also be used with the regulatory elements of the invention. As used herein the term "selectable marker transgene" refers to any transcribable DNA molecule whose expression in a transgenic plant, tissue or cell, or lack thereof, can be screened for or scored in some way. Selectable marker genes, and their associated selection and screening techniques, for use in the practice of the invention are known in the art and include, but are not limited to, transcribable DNA molecules encoding β-glucuronidase (GUS), green fluorescent protein (GFP), proteins that confer antibiotic resistance, and proteins that confer herbicide tolerance. Examples of selectable marker transgenes is provided as SEQ ID NOs:20 and 24.

Cell Transformation

The invention is also directed to a method of producing transformed cells and plants that comprise one or more regulatory elements operably linked to a transcribable DNA molecule.

The term "transformation" refers to the introduction of a DNA molecule into a recipient host. As used herein, the term "host" refers to bacteria, fungi, or plants, including any cells, tissues, organs, or progeny of the bacteria, fungi, or plants. Plant tissues and cells of particular interest include protoplasts, calli, roots, tubers, seeds, stems, leaves, seedlings, embryos, and pollen.

As used herein, the term "transformed" refers to a cell, tissue, organ, or organism into which a foreign DNA molecule, such as a construct, has been introduced. The introduced DNA molecule may be integrated into the genomic DNA of the recipient cell, tissue, organ, or organism such that the introduced DNA molecule is inherited by subsequent progeny. A "transgenic" or "transformed" cell or organism may also include progeny of the cell or organism and progeny produced from a breeding program employing such a transgenic organism as a parent in a cross and exhibiting an altered phenotype resulting from the presence of a foreign DNA molecule. The introduced DNA molecule may also be transiently introduced into the recipient cell such that the introduced DNA molecule is not inherited by subsequent progeny. The term "transgenic" refers to a bacterium, fungus, or plant containing one or more heterologous DNA molecules.

There are many methods well known to those of skill in the art for introducing DNA molecules into plant cells. The process generally comprises the steps of selecting a suitable host cell, transforming the host cell with a vector, and obtaining the transformed host cell. Methods and materials for transforming plant cells by introducing a plant construct into a plant genome in the practice of this invention can include any of the well-known and demonstrated methods. Suitable methods include, but are not limited to, bacterial infection (e.g., *Agrobacterium*), binary BAC vectors, direct delivery of DNA (e.g., by PEG-mediated transformation, desiccation/inhibition-mediated DNA uptake, electroporation, agitation with silicon carbide fibers, and acceleration of DNA coated particles), gene editing (e.g., CRISPR-Cas systems), among others.

Host cells may be any cell or organism, such as a plant cell, algal cell, algae, fungal cell, fungi, bacterial cell, or insect cell. In specific embodiments, the host cells and transformed cells may include cells from crop plants.

A transgenic plant subsequently may be regenerated from a transgenic plant cell of the invention. Using conventional breeding techniques or self-pollination, seed may be produced from this transgenic plant. Such seed, and the resulting progeny plant grown from such seed, will contain the recombinant DNA molecule of the invention, and therefore will be transgenic.

Transgenic plants of the invention can be self-pollinated to provide seed for homozygous transgenic plants of the invention (homozygous for the recombinant DNA molecule) or crossed with non-transgenic plants or different transgenic plants to provide seed for heterozygous transgenic plants of the invention (heterozygous for the recombinant DNA molecule). Both such homozygous and heterozygous transgenic plants are referred to herein as "progeny plants." Progeny plants are transgenic plants descended from the original transgenic plant and containing the recombinant DNA molecule of the invention. Seeds produced using a transgenic plant of the invention can be harvested and used to grow generations of transgenic plants, i.e., progeny plants of the invention, comprising the construct of this invention and expressing a gene of agronomic interest. Descriptions of breeding methods that are commonly used for different crops can be found in one of several reference books, see, e.g., Allard, Principles of Plant Breeding. John Wiley & Sons, NY, U. of CA. Davis, Calif. 50-98 (1960); Simmonds, Principles of Crop Improvement, Longman, Inc., NY, 369-399 (1979); Sneep and Hendriksen, *Plant breeding Perspectives*, Wageningen (ed), Center for Agricultural Publishing and Documentation (1979); Fehr, *Soybeans: Improvement, Production and Uses,* 2nd Edition, Monograph, 16:249 (1987); Fehr, *Principles of Variety Development, Theory and Technique*, (Vol. 1) and Crop Species Soybean (Vol. 2). Iowa State Univ., Macmillan Pub. Co. NY. 360-376 (1987).

The transformed plants may be analyzed for the presence of the gene or genes of interest and the expression level and/or profile conferred by the regulatory elements of the invention. Those of skill in the art are aware of the numerous methods available for the analysis of transformed plants. For example, methods for plant analysis include, but are not limited to.

Southern blots or northern blots, PCR-based approaches, biochemical analyses, phenotypic screening methods, field evaluations, and immunodiagnostic assays. The expression of a transcribable DNA molecule can be measured using TaqMan® (Applied Biosystems. Foster City, Calif.) reagents and methods as described by the manufacturer and PCR cycle times determined using the TaqMan® Testing Matrix. Alternatively, the Invader® (Third Wave Technologies, Madison, Wis.) reagents and methods as described by the manufacturer can be used to evaluate transgene expression.

The invention also provides for parts of a plant of the invention. Plant parts include, but are not limited to, leaves, stems, roots, tubers, seeds, endosperm, ovule, and pollen. Plant parts of the invention may be viable, nonviable, regenerable, and/or non-regenerable. The invention also includes and provides transformed plant cells comprising a DNA molecule of the invention. The transformed or transgenic plant cells of the invention include regenerable and/or non-regenerable plant cells.

The invention also provides a commodity product that is produced from a transgenic plant or part thereof containing the recombinant DNA molecule of the invention. Commodity products of the invention contain a detectable amount of DNA comprising a DNA sequence selected from the group consisting of SEQ ID NOs:1-19 and SEQ ID NO:26. As used herein, a "commodity product" refers to any composition or product which is comprised of material derived from a transgenic plant, seed, plant cell, or plant part containing the recombinant DNA molecule of the invention. Commodity products include but are not limited to processed seeds, grains, plant parts, and meal. A commodity product of the invention will contain a detectable amount of DNA corresponding to the recombinant DNA molecule of the invention. Detection of one or more of this DNA in a sample may be used for determining the content or the source of the commodity product. Any standard method of detection for DNA molecules may be used, including methods of detection disclosed herein.

The invention may be more readily understood through reference to the following examples, which are provided by way of illustration, and are not intended to be limiting of the invention, unless specified. It should be appreciated by those of skill in the art that the techniques disclosed in the following examples represent techniques discovered by the inventors to function well in the practice of the invention. However, those of skill in the art should, in light of the present disclosure, appreciate that many changes can be made in the specific embodiments that are disclosed and still obtain a like or similar result without departing from the spirit and scope of the invention, therefore all matter set forth or shown in the accompanying drawings is to be interpreted as illustrative and not in a limiting sense.

EXAMPLES

Example 1

Design, Synthesis, and Cloning of the Synthetic Regulatory Elements

Novel synthetic transcriptional regulatory elements are synthetic expression elements designed through algorithmic methods. These computationally-designed regulatory elements were chemically synthesized and cloned to make synthetic regulatory expression element groups (EXPs). Well over 1,000 synthetic regulatory elements were designed and assayed in corn protoplasts and stably transformed corn plants to identify those synthetic regulatory elements that provided desired characteristics such as protein expression levels and patterns of expression. The synthetic elements of the present invention provide various patterns of constitutive expression useful in driving expression of many different coding sequences and interfering RNAs of agronomic interest.

The designed synthetic transcriptional regulatory elements do not have extended homology to any known nucleic acid sequences that exist in nature, yet affect transcription of an operably linked coding sequence in the same manner as naturally occurring promoters, leaders, introns, and 3' UTRs. The synthetic EXPs and their corresponding synthetic promoters, leaders, and introns as well as synthetic 3' UTRs are presented in Table 1. The synthetic EXPs were cloned using methods known in the art into binary plant transformation vectors, operably linked to a β-glucuronidase (GUS) coding sequence, and the levels and patterns of expression in stably transformed corn plants were evaluated.

Analysis of the regulatory element TSS and intron/exon splice junctions can be performed using transformed plant tissue. Briefly, the plants were transformed with the plant expression vectors comprising the cloned DNA fragments operably linked to a heterologous transcribable DNA molecule. Next, the 5' RACE System for Rapid Amplification of cDNA Ends. Version 2.0 (Invitrogen, Carlsbad, Calif. 92008), was used to confirm the regulatory element TSS and intron/exon splice junctions by analyzing the DNA sequence of the produced mRNA transcripts. The synthetic 3' UTRs were characterized for their effect on gene expression as well as for proper termination of the transcript.

In addition to the synthetic expression elements, a novel endogenous 3' UTR derived from the *Sorghum bicolor* non-specific lipid-transfer protein 4 gene, T-Sb.Nltp4-1:1:2, is provided herein and is presented as SEQ ID NO:19. T-Sb.Nltp4-1:1:2 was characterized in a similar manner as the synthetic 3' UTRs.

on the type of element being assessed (EXP, Intron, or y UTR). A plasmid used in co-transformation of the protoplasts and normalization of the data was also constructed

TABLE 1

Synthetic transcriptional regulatory expression element groups, promoters, leaders, introns, and 3' UTRs.

| Annotation | SEQ ID NO: | Size (bp) | Description and/or regulatory elements of EXP linked in 5'→3' direction (SEQ ID NOs): |
|---|---|---|---|
| EXP-Zm.GSP850 | 1 | 500 | EXP: P-Zm.GSP850.nno:4 (SEQ ID NO: 2), L-Zm.GSP850.nno:3 (SEQ ID NO: 3) |
| P-Zm.GSP850.nno:4 | 2 | 450 | Promoter |
| L-Zm.GSP850.nno:3 | 3 | 50 | Leader |
| EXP-Zm.GSP850.nno + Zm.GSI153.nno:2 | 4 | 1117 | EXP: P-Zm.GSP850.nno:4 (SEQ ID NO: 2), L-Zm.GSP850.nno:3 (SEQ ID NO: 3), I-Zm.GSI153.nno:1 (SEQ ID NO: 5) |
| I-Zm.GSI153.nno:1 | 5 | 610 | Intron |
| EXP-Zm.GSP990 | 6 | 500 | EXP: P-Zm.GSP990.nno:2 (SEQ ID NO: 7), L-Zm.GSP990.nno:1 (SEQ ID NO: 8) |
| P-Zm.GSP990.nno:2 | 7 | 450 | Promoter |
| L-Zm.GSP990.nno:1 | 8 | 50 | Leader |
| EXP-Zm.GSP990.nno + Zm.GSI197.nno:2 | 9 | 1117 | EXP: P-Zm.GSP990.nno:2 (SEQ ID NO: 7), L-Zm.GSP990.nno:1 (SEQ ID NO: 8), I-Zm.GSI197.nno:1 (SEQ ID NO: 10) |
| I-Zm.GSI197.nno:1 | 10 | 610 | Intron |
| EXP-Zm.GSP850.nno + Zm.GSI140.nno:1 | 11 | 1117 | EXP: P-Zm.GSP850.nno:4 (SEQ ID NO: 2), L-Zm.GSP850.nno:3 (SEQ ID NO: 3), I-Zm.GSI140.nno:1 (SEQ ID NO: 12) |
| I-Zm.GSI140.nno:1 | 12 | 610 | Intron |
| T-Zm.GST9.nno:2 | 13 | 300 | 3' UTR |
| T-Zm.GST18.nno:2 | 14 | 400 | 3' UTR |
| EXP-Zm.GSP850.nno + Zm.DnaK:1 | 15 | 1311 | EXP: P-Zm.GSP850.nno:4 (SEQ ID NO: 2), L-Zm.GSP850.nno:3 (SEQ ID NO: 3), I-Zm.DnaK:1 (SEQ ID NO: 22) |
| EXP-Zm.GSP990.nno + Zm.DnaK:1 | 16 | 1311 | EXP: P-Zm.GSP990.nno:2 (SEQ ID NO: 7), L-Zm.GSP990.nno:1 (SEQ ID NO: 8), I-Zm.DnaK:1 (SEQ ID NO: 22) |
| E-Zm.GSP850 | 17 | 418 | Enhancer |
| E-Zm.GSP990 | 18 | 416 | Enhancer |
| T-Zm.GST43.nno:1 | 26 | 300 | 3' UTR |

Example 2

Analysis of the Synthetic Regulatory Elements Driving GUS in Corn Leaf Protoplasts Corn leaf protoplasts were transformed with vectors, specifically expression vectors containing a test regulatory element driving expression of the β-glucuronidase (GUS) transgene. The resulting transformed corn leaf protoplasts were analyzed for GUS protein expression to assess the effect of the selected regulatory elements on expression.

Corn protoplasts, derived from leaf tissue, were transformed with expression vectors comprising synthetic expression elements. The level and pattern of expression of these synthetic expression element vectors in corn protoplasts was compared to the level and pattern of expression of expression elements known in the art. Separate experiments were conducted to assess the activity of the EXP's. EXP-Zm.GSP850 (SEQ ID NO:1) and EXP-Zm.GSP990 (SEQ ID NO:6), the introns I-Zm.GSI153.nno:1 (SEQ ID NO:5) and I-Zm.GSI197.nno:1 (SEQ ID NO: 10), and the 3' UTR's, T-Zm.GST9.nno:2 (SEQ ID NO: 13) and T-Zm.GST18.nno:2 (SEQ ID NO: 14). The expression elements were cloned into expression vectors and operably linked to a GUS coding sequence, GOI-Ec.uidA+St.LS1:1:1 (SEQ ID NO:24), that comprised a processable intron. The control expression vectors comprised different configurations of known expression elements which varied dependent using methods known in the art. It comprised a transgene cassette comprised of the EXP, EXP-CaMV.35S (SEQ ID NO:21) operably linked 5' to a coding sequence encoding the NanoLuc® luciferase fluorescent protein (Promega, Madison. Wis. 53711), herein referred to as Niue (SEQ ID NO:25), which was operably linked 5' to a 3' UTR, T-Os.LTP: 1 (SEQ ID NO:23).

Corn leaf protoplasts were transformed using a PEG-based transformation method, similar to those known in the art. Protoplast cells were transformed in a ninety six (96) well format. Twelve (12) micrograms of the test vector DNA or control vector DNA, and six (6) micrograms of the NanoLuc® vector DNA were used to transform $3.2 \times 10^5$ protoplasts per well. After transformation, the protoplasts were incubated at 25° C. in the dark for sixteen to twenty hours. Following incubation, the protoplasts were lysed and the lysate was used for measuring luciferase and GUS expression. To lyse the cells, the cells in the plate were pelleted through centrifugation, washed, resuspended in a smaller volume, and transferred to strip well tubes. The lubes were centrifuged again and supernatant was aspirated leaving the protoplast cell pellet behind. The cell pellet was resuspended in QB buffer (100 mM $KPO_4$, pH 7.8; 1 mM EDTA; 1% Triton X-100; 10% Glycerol; 1 mM DTT). The cells were lysed by vigorously pipetting the cells several times, vortexing the tubes, and letting the tubes incubate on ice for five minutes. The lysate was then centrifuged to pellet the cell debris. The resulting lysate was then transferred to a clean plate.

Luciferase activity was assayed using the Nano-Glo® Luciferase Assay Substrate (Promega, Madison, Wis. 53711) in QB buffer. In short, a small volume of lysate, QB buffer, and the Nano-Glo® Luciferase Assay Substrate/QB solution were mixed together in white, ninety six (96) well plates. Fluorescence was then measured using a PHERAstar® plate reader (BMG LABTECH Inc., Cary, N.C. 27513).

GUS activity was assayed using the fluorogenic substrate 4-methylcumbellifcryl-β-D-glucuronide (MUG) in a total reaction volume of fifty (50) microliters. The reaction product, 4-methylumbelliferone (4-MU), is maximally fluorescent at high pH, where the hydroxyl group is ionized. Addition of a basic solution of sodium carbonate simultaneously stops the assay and adjusts the pH for quantifying the fluorescent product. An aliquot of lysate was mixed with an aliquot of MUG dissolved in QB buffer and incubated at 37° C. A small aliquot of the lysate/MUG reaction mixture was removed and added to a stop buffer at three different time points: (1) immediately after mixing the lysate/MUG reaction as "Time zero minutes"; (2) twenty minutes; and (3) sixty minutes. Fluorescence was measured with excitation at 355 nm, emission at 460 nm using a using a PHERAstar® plate reader (BMG LABTECH Inc., Cary, N.C. 27513). The level of expression is expressed as "nM MUG hydrolyzed" which is derived from the-in-plate standard curve.

For each plate, each construct is transformed in four (4) to eight (8) wells. An aliquot was taken out of each transformation for the MUG assay and "nM MUG hydrolyzed" was derived from the in-plate-standard curve. An aliquot was also taken out of each transformation for the NanoLuc® reading (NanoLuc® RLU). The mean nM MUG hydrolyzed/NanoLuc® RLU for each construct was normalized with respect to the EXP-CaMV.35S/I-Zm.DnaK:1/T-Os.LTP: 1 construct which is set to 100%.

Analysis of GUS Expression in Corn Leaf Protoplasts Driven by the Synthetic EXP, EXP-Zm.GSP850.

Corn leaf protoplast cells were transformed with expression vectors that were constructed using methods known in the art comprising expression elements driving GUS expression. Two (2) test expression vectors comprised transgene cassettes comprising the synthetic EXP, EXP-Zm.GSP850 (SEQ ID NO:1). The synthetic EXP-Zm.GSP850 is comprised of a synthetic promoter, P-Zm.GSP850.nno:4 (SEQ ID NO:2), operably linked 5' to a synthetic leader. L-Zm.GSP850.nno:3 (SEQ ID NO:3). The first test vector comprised EXP-Zm.GSP850, operably linked 5' to a coding sequence encoding GUS (SEQ ID NO:24) which comprised a processable intron, which was operably linked 5' to the 3' UTR, T-Os.LTP:1 (SEQ ID NO:23). The second transgene cassette comprised EXP-Zm.GSP850, operably linked 5' to the intron I-Zm.DnaK:1 (SEQ ID NO:22), operably linked 5' to the GUS coding sequence, which was operably linked 5' to the 3' UTR, T-Os.LTP:1.

Three (3) control expression vectors were also constructed and used to transform corn leaf protoplasts. The first control expression vector comprised a promoterless transgene cassette and was comprised of the intron. I-Zm.DnaK:1, operably linked 5' to the GUS coding sequence, which was operably linked 5' to the 3' UTR, T-Os.LTP:1. The second control vector comprised an intronless transgene cassette and was comprised of the EXP, EXP-CaMV.35S (SEQ ID NO:21), operably linked 5' to the GUS coding sequence, which was operably linked 5' to the 3' UTR, T-Os.LTP:1. The third control vector comprised a transgene cassette which comprised the EXP, EXP-CaMV.35S, operably linked 5' to the intron I-Zm.DnaK:1, operably linked 5' to the GUS coding sequence, which was operably linked 5' to the 3' UTR, T-Os.LTP:1.

Corn leaf protoplasts were transformed with all five (5) vectors. Transformation and lyses of the protoplast cells were performed as described herein. Luciferase and GUS expression were assayed as described herein. Table 2 shows the Mean GUS expression assayed and is expressed as a percentage of expression relative to the third control expression vector that comprises EXP-CaMV.35S and I-Zm.DnaK:1 driving GUS.

TABLE 2

Mean percent GUS expression of corn leaf protoplasts transformed with test and control vectors.

| Plate ID | Promoter | Intron | Mean | SD | Reps |
|---|---|---|---|---|---|
| 39 | No Promoter | I-Zm.DnaK:1 | 0.1 | 0.337 | 6 |
| 54 | No Promoter | I-Zm.DnaK:1 | 0.4 | 0.315 | 8 |
| 95 | No Promoter | I-Zm.DnaK:1 | 0.1 | 0.534 | 8 |
| 103 | No Promoter | I-Zm.DnaK:1 | 0.5 | 0.149 | 8 |
| 39 | EXP-CaMV.35S | No Intron | 48.3 | 2.018 | 6 |
| 54 | EXP-CaMV.35S | No Intron | 46.5 | 3.949 | 8 |
| 95 | EXP-CaMV.35S | No Intron | 46.8 | 4.369 | 8 |
| 103 | EXP-CaMV.35S | No Intron | 40 | 3.333 | 8 |
| 39 | EXP-CaMV.35S | I-Zm.DnaK:1 | 100 | 5.117 | 6 |
| 54 | EXP-CaMV.35S | I-Zm.DnaK:1 | 100 | 6.465 | 8 |
| 95 | EXP-CaMV.35S | I-Zm.DnaK:1 | 100 | 18.603 | 8 |
| 103 | EXP-CaMV.35S | I-Zm.DnaK:1 | 100 | 5.164 | 8 |
| 95 | EXP-Zm.GSP850 | No Intron | 14 | 1.844 | 8 |
| 103 | EXP-Zm.GSP850 | No Intron | 8.4 | 0.336 | 8 |
| 39 | EXP-Zm.GSP850 | I-Zm.DnaK:1 | 19 | 0.732 | 4 |
| 54 | EXP-Zm.GSP850 | I-Zm.DnaK:1 | 22 | 1.954 | 8 |

As can be seen in Table 2 above, EXP-Zm.GSP850 (SEQ ID NO:1) was able to drive GUS transgene expression in corn leaf protoplasts when compared to corn leaf protoplast cells transformed with a promoterless construct.

Analysis of GUS Expression in Corn Leaf Protoplasts Driven by the Synthetic EXP, EXP-Zm.GSP990.

Corn leaf protoplast cells were transformed with expression vectors that were constructed comprising expression elements driving GUS expression. A test expression vector comprised a transgene cassette which comprised the synthetic EXP, EXP-Zm.GSP990 (SEQ ID NO:6), operably linked 5' to the intron I-Zm.DnaK:1 (SEQ ID NO:22), operably linked 5' to a coding sequence encoding GUS (SEQ ID NO:20), which was operably linked 5' to the 3' UTR, T-Os.LTP:1. The synthetic EXP-Zm.GSP990 (SEQ ID NO:6) is comprised of a synthetic promoter, P-Zm.GSP990.nno:2 (SEQ ID NO:7), operably linked 5' to a synthetic leader. L-Zm.GSP990.nno: 1 (SEQ ID NO:8). Three control expression vectors were also transformed into corn leaf protoplasts and were constructed as described above. Table 3 shows the mean percent expression relative to the third control expression vector that comprises EXP-CaMV.35S and I-Zm.DnaK:1 driving GUS.

TABLE 3

Mean percent GUS expression of corn leaf protoplasts transformed with test and control vectors.

| Plate ID | Promoter | Intron | Mean | SD | Reps |
|---|---|---|---|---|---|
| 71 | No Promoter | I-Zm.DnaK:1 | 0.3 | 0.125 | 6 |
| 108 | No Promoter | I-Zm.DnaK:1 | −0.6 | 1.211 | 8 |
| 71 | EXP-CaMV.35S | No Intron | 45.1 | 7.791 | 6 |
| 108 | EXP-CaMV.35S | No Intron | 39.9 | 2.636 | 8 |
| 71 | EXP-CaMV.35S | I-Zm.DnaK:1 | 100 | 13.591 | 6 |

TABLE 3-continued

Mean percent GUS expression of corn leaf protoplasts transformed with test and control vectors.

| Plate ID | Promoter | Intron | Mean | SD | Reps |
|---|---|---|---|---|---|
| 108 | EXP-CaMV.35S | I-Zm.DnaK:1 | 100 | 7.425 | 8 |
| 71 | EXP-Zm.GSP990 | I-Zm.DnaK:1 | 52.3 | 13.658 | 4 |
| 108 | EXP-Zm.GSP990 | I-Zm.DnaK:1 | 45.2 | 5.468 | 8 |

As can be seen in Table 3, EXP-Zm.GSP990 (SEQ ID NO:6) was able to drive GUS transgene expression in corn leaf protoplasts when compared to corn leaf protoplast cells transformed with a promoterless construct.

Analysis of Enhancement of GUS Expression by the Synthetic Intron, I-Zm.GSI153.nno:1

Corn leaf protoplast cells were transformed with expression vectors that were constructed comprising expression elements driving GUS expression. A test expression vector was used to assay the enhancement of GUS expression from the synthetic intron, I-Zm.GSI153.nno:1 (SEQ ID NO:5), driven by EXP-CaMV.35. The transgene cassette comprised the EXP, EXP-CaMV.35 operably linked 5' to the synthetic intron, I-Zm.GSI153.nno:1 (SEQ ID NO:5), operably linked 5' to a coding sequence encoding GUS (SEQ ID NO:24), which was operably linked 5' to the 3' UTR, T-Os.LTP:1. Two control expression vectors were also constructed and used to transform corn leaf protoplasts. The first control expression vector comprised an intronless transgene cassette and was comprised of the EXP. EXP-CaMV.35S, operably linked 5' to the GUS coding sequence, which was operably linked 5' to the 3' UTR, T-Os.LTP:1. The second control vector comprised a transgene cassette which comprised the EXP, EXP-CaMV.35S, operably linked 5' to the intron I-Zm.DnaK:1, operably linked 5' to the GUS coding sequence, which was operably linked 5' to the 3' UTR. T-Os.LTP:1. Table 4 shows the mean percent expression relative to the second control expression vector that comprises both EXP-CaMV.35S and I-Zm.DnaK:1 driving GUS.

TABLE 4

Mean percent GUS expression of corn leaf protoplasts transformed with test and control vectors.

| Plate ID | Promoter | Intron | Mean | SD | Reps |
|---|---|---|---|---|---|
| 10 | EXP-CaMV.35S | No Intron | 52.8 | 8.428 | 6 |
| 13 | EXP-CaMV.35S | No Intron | 44.4 | 4.586 | 8 |
| 10 | EXP-CaMV.35S | I-Zm.DnaK:1 | 100 | 16.646 | 6 |
| 13 | EXP-CaMV.35S | I-Zm.DnaK:1 | 100 | 13.123 | 8 |
| 10 | EXP-CaMV.35S | I-Zm.GSI153.nno:1 | 83 | 5.601 | 4 |
| 13 | EXP-CaMV.35S | I-Zm.GSI153.nno:1 | 83.6 | 7.596 | 8 |

As can be seen in Table 4, the synthetic intron, I-Zm.GSI153.nno:1 (SEQ ID NO:5), enhanced GUS transgene expression in corn leaf protoplasts driven by EXP-CaMV.35S when compared to the intronless control expression vector.

Analysis of Enhancement of GUS Expression by the Synthetic Intron, I-Zm.GSI197.nno:1

Corn leaf protoplast cells were transformed with expression vectors that were constructed comprising expression elements driving GUS expression. A test expression vector was used to assay the enhancement of GUS expression from the synthetic intron, I-Zm.GSI197.nno:1 (SEQ ID NO: 10), driven by EXP-CaMV.35. The transgene cassette comprised the EXP, EXP-CaMV.35 operably linked 5' to the synthetic intron, I-Zm.GSI197.nno:1, operably linked 5' to a coding sequence encoding GUS (SEQ ID NO:24), which was operably linked 5' to the 3' UTR, T-Os.LTP:1. Three control expression vectors were also constructed and used to transform corn leaf protoplasts. The first control expression vector comprised a promoterless transgene cassette and was comprised of the intron, I-Zm.DnaK:1, operably linked 5' to the GUS coding sequence, which was operably linked 5' to the 3' UTR, T-Os.LTP:1. The second control vector comprised an intronless transgene cassette and was comprised of the EXP, EXP-CaMV.35S, operably linked 5' to the GUS coding sequence, which was operably linked 5' to the 3' UTR, T-Os.LTP:1.

The third control vector comprised a transgene cassette which comprised the EXP, EXP-CaMV.35S, operably linked 5' to the intron I-Zm.DnaK:1, operably linked 5' to the GUS coding sequence, which was operably linked 5' to the 3' UTR, T-Os.LTP:1. Table 5 shows the mean percent expression relative to the third control expression vector that comprises both EXP-PGP-25 T1 CaM V.35S and I-Zm.DnaK:1 driving GUS.

TABLE 5

Mean percent GUS expression of corn leaf protoplasts transformed with test and control vectors.

| Plate ID | Promoter | Intron | Mean | SD | Reps |
|---|---|---|---|---|---|
| 125 | No Promoter | I-Zm.DnaK:1 | 1.1 | 0.317 | 6 |
| 146 | No Promoter | I-Zm.DnaK:1 | 0.6 | 0.101 | 8 |
| 125 | EXP-CaMV.35S | No Intron | 43.8 | 4.081 | 6 |
| 146 | EXP-CaMV.35S | No Intron | 41 | 3.666 | 8 |
| 125 | EXP-CaMV.35S | I-Zm.DnaK:1 | 100 | 11.287 | 6 |
| 146 | EXP-CaMV.35S | I-Zm.DnaK:1 | 100 | 8.506 | 8 |
| 125 | EXP-CaMV.35S | I-Zm.GSI197.nno:1 | 150 | 12.451 | 4 |
| 146 | EXP-CaMV.35S | I-Zm.GSI197.nno:1 | 109.8 | 8.001 | 8 |

As can be seen in Table 5, the synthetic intron. I-Zm.GSI197.nno:1 (SEQ ID NO: 10), enhanced GUS transgene expression in corn leaf protoplasts driven by EXP-CaMV.35S when compared to the intronless control expression vector. The enhancement of expression was greater than that imparted by the intron, I-Zm.DnaK:1 when compared to the third control expression vector which comprised the EXP, EXP-CaMV.35S, operably linked 5' to the intron I-Zm.DnaK:1.

Analysis of Enhancement of GUS Expression by the Synthetic 3' UTRs, T-Zm.GST9.nno:2 and T-Zm.GST18.nno:2.

Corn leaf protoplast cells were transformed with expression vectors that were constructed comprising expression elements driving GUS expression. Two test vectors comprised a transgene cassette used for the analysis of GUS expression enhancement imparted by the 3' UTRs, T-Zm.GST9.nno:2 (SEQ ID NO: 13) and T-Zm.GST18.nno:2 (SEQ ID NO: 14) and was comprised of EXP-CaMV.35S operably linked 5' to the intron I-Zm.DnaK:1, operably linked 5' to a coding sequence encoding GUS (SEQ ID NO:24), which was operably linked 5' to the either the 3' UTR, T-Zm.GST9.nno:2 (SEQ ID NO:13) or the 3' UTR, T-Zm.GST18.nno:2 (SEQ ID NO: 14). Three control expression vectors were also constructed, as described above, and used to transform corn leaf protoplasts. Table 6 shows the mean percent expression relative to the third control expression vector that comprises both EXP-CaMV.35S and I-Zm.DnaK:1 driving GUS.

TABLE 6

Mean percent GUS expression of corn leaf protoplasts transformed with test and control vectors.

| Plate ID | Promoter | Intron | 3' UTR | Mean | SD | Reps |
|---|---|---|---|---|---|---|
| 119 | No Promoter | I-Zm.DnaK:1 | T-Os.LTP:1 | 3.5 | 2.163 | 8 |
| 184 | No Promoter | I-Zm.DnaK:1 | T-Os.LTP:1 | 0.1 | 0.205 | 6 |
| 185 | No Promoter | I-Zm.DnaK:1 | T-Os.LTP:1 | 0 | 0.331 | 8 |
| 328 | No Promoter | I-Zm.DnaK:1 | T-Os.LTP:1 | 10.2 | 3.017 | 6 |
| 119 | EXP-CaMV.35S | No Intron | T-Os.LTP:1 | 45.5 | 3.729 | 8 |
| 184 | EXP-CaMV.35S | No Intron | T-Os.LTP:1 | 33.7 | 2.719 | 6 |
| 185 | EXP-CaMV.35S | No Intron | T-Os.LTP:1 | 33.6 | 2.576 | 8 |
| 328 | EXP-CaMV.35S | No Intron | T-Os.LTP:1 | 48.8 | 3.69 | 6 |
| 119 | EXP-CaMV.35S | I-Zm.DnaK:1 | T-Os.LTP:1 | 100 | 7.305 | 8 |
| 184 | EXP-CaMV.35S | I-Zm.DnaK:1 | T-Os.LTP:1 | 100 | 6.91 | 6 |
| 185 | EXP-CaMV.35S | I-Zm.DnaK:1 | T-Os.LTP:1 | 100 | 6.308 | 8 |
| 328 | EXP-CaMV.35S | I-Zm.DnaK:1 | T-Os.LTP:1 | 100 | 5.989 | 6 |
| 184 | EXP-CaMV.35S | I-Zm.DnaK:1 | T-Zm.GST9.nno:2 | 202.5 | 17.582 | 4 |
| 119 | EXP-CaMV.35S | I-Zm.DnaK:1 | T-Zm.GST18.nno:2 | 483.2 | 40.613 | 8 |
| 185 | EXP-CaMV.35S | I-Zm.DnaK:1 | T-Zm.GST18.nno:2 | 254.5 | 18.347 | 8 |
| 328 | EXP-CaMV.35S | I-Zm.DnaK:1 | T-Zm.GST18.nno:2 | 307.4 | 17.772 | 4 |

As can be Seen in Table 6, the 3' UTRs, T-Zm.GST9.nno:2 (SEQ ID NO:13) and T-Zm.GST18.nno:2 (SEQ ID NO: 14) Enhanced GUS Expression Relative to the Controls in Corn Leaf Protoplasts Example 3

Analysis of GUS Expression Driven by the Synthetic EXPs, EXP-Zm.GSP850.nno+Zm.GSI153.nno:2 and EXP-Zm.GSP850.nno+Zm.GSI140.nno:1 in Stably Transformed LH244 Variety Corn Plants Corn plants were transformed with a vector, specifically a plant expression vector containing test regulatory elements driving expression of the β-glucuronidase (GUS) transgene. The resulting plants were analyzed for GUS protein expression, to assess the effect of the selected regulatory element on expression.

Corn plants were transformed with plant GUS expression constructs. The regulatory elements were cloned into a base plant expression vector using standard methods known in the art. The resulting plant expression vectors contained a left border region from *Agrobacterium tumefaciens* (B-AGRtu.left border), a first transgene selection cassette used for selection of transformed plant cells that confers resistance to the herbicide glyphosate; a second transgene cassette to assess the activity of the synthetic regulatory elements, which comprised either the synthetic EXP, EXP-Zm.GSP850.nno+Zm.GSI153.nno:2 (SEQ ID NO:4) or EXP-Zm.GSP850.nno+Zm.GSI140.nno:1 (SEQ ID NO:11) operably linked 5' to a synthetic coding sequence designed for expression in a plant cell encoding β-glucuronidase (GUS. GOI-Ec.uidA+St.LS1.nno:1, SEQ ID NO:20) containing a processable intron derived from the potato light-inducible tissue-specific ST-LS1 gene (Genbank Accession: X04753), operably linked 5' to a 3' termination region. T-Sb.Nltp4-1:1:2 (SEQ ID NO:19); and a right border region from *Agrobacterium tumefaciens* (B-AGRtu.right border). The synthetic EXP, EXP-Zm.GSP850.nno+ Zm.GSI153.nno:2 (SEQ ID NO:4) is comprised of a synthetic promoter, P-Zm.GSP850.nno:4 (SEQ ID NO:2), operably linked 5' to a synthetic leader, L-Zm.GSP850.nno:3 (SEQ ID NO:3), which is operably linked 5' to a synthetic intron, I-Zm.GSI153.nno:1 (SEQ ID NO:5). The synthetic EXP, EXP-Zm.GSP850.nno+Zm.GSI140.nno:1 (SEQ ID NO:11) is comprised of a synthetic promoter. P-Zm.GSP850.nno:4 (SEQ ID NO:2), operably linked 5' to a synthetic leader. L-Zm.GSP850.nno:3 (SEQ ID NO:3), which is operably linked 5' to a synthetic intron, I-Zm.GSI140.nno:1 (SEQ ID NO:12).

Corn variety LH244 plant cells were transformed using the binary transformation vector construct described above by *Agrobacterium*-mediated transformation, as is well known in the art. The resulting transformed plant cells were induced to form whole corn plants.

Qualitative and quantitative GUS analysis was used to evaluate expression element activity in selected plant organs and tissues in transformed plants. For qualitative analysis of GUS expression by histochemical staining, whole-mount or sectioned tissues were incubated with GUS staining solution containing 1 mg/mL of X-Gluc (5-bromo-4-chloro-3-indo-lyl-b-glucuronide) for 5 h at 37° C. and de-stained with 35% EtOH and 50% acetic acid. Expression of GUS was qualitatively determined by visual inspection of selected plant organs or tissues for blue coloration under a dissecting or compound microscope.

For quantitative analysis of GUS expression by enzymatic assays, total protein was extracted from selected tissues of transformed corn plants. One to two micrograms of total protein was incubated with the fluorogenic substrate, 4-methyleumbelliferyl-β-D-glucuronide (MUG) at 1 mM concentration in a total reaction volume of 50 microliters. After 1 h incubation at 37° C., the reaction was stopped by adding 350 microliters of 200 mM sodium bicarbonate solution. The reaction product, 4-methlyumbelliferone (4-MU), is maximally fluorescent at high pH, where the hydroxyl group is ionized. Addition of the basic sodium carbonate solution simultaneously slops the assay and adjusts the pH for quantifying the fluorescent product 4-MU. The amount of 4-MU formed was estimated by measuring its fluorescence using a FLUOstar Omega Microplate Reader (BMG LABTECH) (excitation at 355 nm, emission at 460 nm). GUS activity values are provided in nmoles of 4-MU/hour/mg total protein.

The following tissues were sampled for GUS expression in the $R_0$ generation: V4 stage Leaf and Root; V7 stage Leaf and Root; VT stage Leaf, Root, and Flower/Anther, R1 stage Cob/Silk; and R3 stage Seed Embryo and Seed Endosperm 21 days after pollination (DAP). Table 7 shows the mean quantitative GUS expression values for each of the synthetic EXPs.

TABLE 7

Mean quantitative GUS expression in stably transformed LH244 variety corn plants driven by the synthetic EXPs, EXP-Zm.GSP850.nno + Zm.GSI153.nno:2 and EXP-Zm.GSP850.nno + Zm.GSI140.nno:1.

| Stage | Organ | EXP-Zm.GSP850.nno + Zm.GSI153.nno:2 (SEQ ID NO: 4) | EXP-Zm.GSP850.nno + Zm.GSI140.nno:1 (SEQ ID NO: 11) |
|---|---|---|---|
| V4 | Leaf | 694 | 642 |
|    | Root | 870 | 116 |
| V7 | Leaf | 1423 | 1265 |
|    | Root | 476 | 521 |
| VT | Leaf | 2646 | 344 |
|    | Root | 424 | 70 |
|    | Flower/Anther | 5465 | 1267 |
| R1 | Cob/Silk | 3618 | 1116 |
| R3 | Seed Embryo 21 DAP | 260 | 224 |
|    | Seed Endosperm 21 DAP | 2648 | 1140 |

As can be seen in Table 7, the synthetic GSP850 promoter and leader (P-Zm.GSP850.nno:4 (SEQ ID NO:2) and L-Zm.GSP850.nno:3 (SEQ ID NO:3)) drove constitutive expression of GUS in stably transformed LH244 variety corn plants. Molecular analysis of the transcript start site demonstrated a consistent TSS for the GSP850 promoter and leader. The synthetic introns, I-Zm.GSI153.nno:1 (SEQ ID NO:5) and I-Zm.GSI140.nno:1 (SEQ ID NO: 12) affected expression differently in the different tissues sampled. Molecular analysis of the intron splice sites demonstrated consistent processing of the synthetic introns. Overall enhancement of GUS expression was higher in most tissue samples from plants comprising I-Zm.GSI153.nno:1 (SEQ ID NO:5), with the exception of V4 stage leaf, V7 stage root, and R3 seed embryo where GUS expression levels were relatively similar. Enhancement of expression imparted by I-Zm.GSI153.nno:1 (SEQ ID NO:5) relative to I-Zm.GSI140.nno:1 (SEQ ID NO:12) was approximately 7.5-fold higher in V4 root, 7.7 fold higher in VT leaf, 6.0 fold higher in VT root, 4.3 fold higher in VT flower/anther, 3.2 fold higher in R1 cob/silk, and 2.3 fold higher in R3 seed endosperm.

Example 4

Analysis of GUS Expression Driven by the Synthetic EXPs EXP-Zm.GSP850.nno+Zm.DnaK:1, EXP-Zm.GSP850.nno+Zm.GSI153.nno:2, and EXP-Zm.GSP850.nno+Zm.GSI140.nno:1 in Stably Transformed 01DKD2 Variety Corn Plants Corn plants were transformed with a vector, specifically a plant expression vector containing test regulatory elements driving expression of the β-glucuronidase (GUS) transgene. The resulting plants were analyzed for GUS protein expression, to assess the effect of the selected regulatory element on expression.

Corn plants were transformed with plant GUS expression constructs. The regulatory elements were cloned into a base plant expression vector using standard methods known in the art. The resulting plant expression vectors contained a left border region from Agrobacterium tumefaciens (B-AGRtu.left border), a first transgene selection cassette used for selection of transformed plant cells that confers resistance to the herbicide glyphosate; a second transgene cassette to assess the activity of the regulatory elements, which comprised either the synthetic EXP, EXP-Zm.GSP850.nno+Zm.DnaK:1 (SEQ ID NO: 15), EXP-Zm.GSP850.nno+Zm.GSI153.nno:2 (SEQ ID NO:4) or EXP-Zm.GSP850.nno+Zm.GSI140.nno:1 (SEQ ID NO: 11) operably linked 5' to a synthetic coding sequence designed for expression in a plant cell encoding β-glucuronidase (GUS, GOI-Ec.uidA+St.LS1.nno: 1, SEQ ID NO:20) containing a processable intron derived from the potato light-inducible tissue-specific ST-LS1 gene (Genbank Accession: X04753), operably linked 5' to a 3' termination region, T-Sb.Nltp4-1:1:2 (SEQ ID NO: 19); and a right border region from Agrobacterium tumefaciens (B-AGRtu.right border). The synthetic EXP, EXP-Zm.GSP850.nno+Zm.DnaK:1 (SEQ ID NO: 15) is comprised of a synthetic promoter, P-Zm.GSP850.nno:4 (SEQ ID NO:2), operably linked 5' to a synthetic leader, L-Zm.GSP850.nno:3 (SEQ ID NO:3), which is operably linked 5' to an intron, I-Zm.DnaK:1 (SEQ ID NO: 22). The synthetic EXPs, EXP-Zm.GSP850.nno+Zm.GSI153.nno:2 (SEQ ID NO:4) and EXP-Zm.GSP850.nno+Zm.GSI140.nno:1(SEQ ID NO:11) are described in Example 3.

Corn variety 01DKD2 plant cells were transformed using the binary transformation vector construct described above by Agrobacterium-mediated transformation, as is well known in the art. The resulting transformed plant cells were induced to form whole corn plants. Qualitative and quantitative GUS expression was assayed as described in Example 3. Table 8 shows the mean quantitative GUS expression values for each of the synthetic EXPs.

TABLE 8

Mean quantitative GUS expression in stably transformed 01DKD2 variety corn plants driven by the synthetic EXPs EXP-Zm.GSP850.nno + Zm.DnaK:1, EXP-Zm.GSP850.nno + Zm.GSI153.nno:2, and EXP-Zm.GSP850.nno + Zm.GSI140.nno:1.

| Stage | Organ | EXP-Zm.GSP850.nno + Zm.DnaK:1 (SEQ ID NO: 15) | EXP-Zm.GSP850.nno + Zm.GSI153.nno:2 (SEQ ID NO: 4) | EXP-Zm.GSP850.nno + Zm.GSI140.nno:1 (SEQ ID NO: 11) |
|---|---|---|---|---|
| V4 | Leaf | 208 | 374 | 519 |
|    | Root | 36 | 606 | 341 |
| V7 | Leaf | 314 | 539 | 619 |
|    | Root | 22 | 1158 | 303 |

TABLE 8-continued

Mean quantitative GUS expression in stably transformed 01DKD2 variety corn plants driven by the synthetic EXPs EXP-Zm.GSP850.nno + Zm.DnaK:1, EXP-Zm.GSP850.nno + Zm.GSI153.nno:2, and EXP-Zm.GSP850.nno + Zm.GSI140.nno:1.

| Stage | Organ | EXP-Zm.GSP850.nno + Zm.DnaK:1 (SEQ ID NO: 15) | EXP-Zm.GSP850.nno + Zm.GSI153.nno:2 (SEQ ID NO: 4) | EXP-Zm.GSP850.nno + Zm.GSI140.nno:1 (SEQ ID NO: 11) |
|---|---|---|---|---|
| VT | Leaf | 26 | 610 | 630 |
|  | Root | 32 | 770 | 797 |
|  | Flower/Anther | 104 | 797 | 1121 |
| R1 | Cob/Silk | 160 | 1139 | 1312 |
| R3 | Seed Embryo 21 DAP | 31 | 188 | 723 |
|  | Seed Endosperm 21 DAP | 98 | 1490 | 1635 |

As can be seen in Table 8, the synthetic GSP850 promoter and leader (P-Zm.GSP850.nno:4 (SEQ ID NO:2) and L-Zm.GSP850.nno:3 (SEQ ID NO:3)) drove constitutive expression of GUS in stably transformed LH244 variety corn plants. The synthetic introns, I-Zm.GSI153.nno:1 (SEQ ID NO:5) and I-Zm.GSI140.nno:1 (SEQ ID NO: 12) enhanced expression relative to the intron, I-Zm.DnaK:1 (SEQ ID NO:22) in all tissues assayed.

Example 5

Analysis of GUS Expression Driven by the Synthetic EXPs EXP-Zm.GSP990.nno+Zm.DnaK:1 and EXP-Zm.GSP990.nno+Zm.GSI197.nno:2 in Stably Transformed 01DKD2 Variety Corn Plants Corn plants were transformed with a vector, specifically a plant expression vector containing test regulatory elements driving expression of the β-glucuronidase (GUS) transgene. The resulting plants were analyzed for GUS protein expression, to assess the effect of the selected regulatory element on expression.

Corn plants were transformed with plant GUS expression constructs. The regulatory elements were cloned into a base plant expression vector using standard methods known in the art. The resulting plant expression vectors contained a left border region from Agrobacterium tumefaciens (B-AGRtu.left border), a first transgene selection cassette used for selection of transformed plant cells that confers resistance to the herbicide glyphosate; a second transgene cassette to assess the activity of the regulatory elements, which comprised either the synthetic EXP EXP-Zm.GSP990.nno+Zm.DnaK:1 (SEQ ID NO: 16) or EXP-Zm.GSP990.nno+Zm.GSI197.nno:2 (SEQ ID NO:9) operably linked 5' to a synthetic coding sequence designed for expression in a plant cell encoding β-glucuronidase (GUS, GOI-Ec.uidA+St.LS1.nno:1, SEQ ID NO:20) containing a processable intron derived from the potato light-inducible tissue-specific ST-LS1 gene (Genbank Accession: X04753), operably linked 5' to a 3' termination region, T-Sb.Nltp4-1:1:2 (SEQ ID NO:19); and a right border region from Agrobacterium tumefaciens (B-AGRtu.right border). The synthetic EXP EXP-Zm.GSP990.nno+Zm.GSI197.nno:2 (SEQ ID NO:9) is comprised of a synthetic promoter. P-Zm.GSP990.nno:2 (SEQ ID NO:7), operably linked 5' to a synthetic leader, L-Zm.GSP990.nno: 1 (SEQ ID NO:8), which is operably linked 5' to a synthetic intron, I-Zm.GSI197.nno:1 (SEQ ID NO:10). The synthetic EXP EXP-Zm.GSP990.nno+Zm.DnaK:1 (SEQ ID NO: 16) is comprised of a synthetic promoter, P-Zm.GSP990.nno:2 (SEQ ID NO:7), operably linked 5' to a synthetic leader, L-Zm.GSP990.nno: 1 (SEQ ID NO:8), which is operably linked 5' to an intron, I-Zm.DnaK:1 (SEQ ID NO:22).

Corn variety 01DKD2 plant cells were transformed using the binary transformation vector construct described above by Agrobacterium-mediated transformation, as is well known in the art. The resulting transformed plant cells were induced to form whole corn plants. Qualitative and quantitative GUS expression was assayed as previously described in Example 3. Table 9 shows the mean quantitative GUS expression values for each of the synthetic EXPs, wherein "ND" indicates not determined.

TABLE 9

Mean quantitative GUS expression in stably transformed 01DKD2 variety corn plants driven by the synthetic EXPs EXP-Zm.GSP990.nno + Zm.DnaK:1 and EXP-Zm.GSP990.nno + Zm.GSI197.nno:2.

| Stage | Organ | EXP-Zm.GSP990.nno + Zm.DnaK:1 (SEQ ID NO: 16) | EXP-Zm.GSP990.nno + Zm.GSI197.nno:2 (SEQ ID NO: 9) |
|---|---|---|---|
| V4 | Leaf | 99 | 75 |
|  | Root | 32 | 33 |
| V7 | Leaf | 226 | 138 |
|  | Root | 29 | 40 |
| VT | Leaf | 140 | 61 |
|  | Root | 55 | 96 |
|  | Flower/Anther | 87 | 231 |
| R1 | Cob/Silk | 39 | 35 |
| R3 | Seed Embryo 21 DAP | ND | 21 |
|  | Seed Endosperm 21 DAP | ND | 22 |

As can be seen, the synthetic GSP990 promoter and leader (P-Zm.GSP990.nno:2 (SEQ ID NO:7) and L-Zm.GSP990.nno: 1 (SEQ ID NO:8)) drove expression of GUS. Molecular analysis of the transcript start site demonstrated a consistent TSS for the GSP990 promoter and leader. The synthetic intron, I-Zm.GSI197.nno:1 (SEQ ID NO: 10) attenuated expression in some tissues, while enhancing expression in other tissues, relative to the intron, I-Zm.DnaK:1 (SEQ ID NO:22). For example, expression of GUS was attenuated in leaf at V4, V7, and VT stage. GUS expression was slightly enhanced in the V7 and VT root, relative to I-Zm.DnaK:1. Flower/anther expression was enhanced approximately 2.7 fold by I-Zm.GSI197.nno:1

(SEQ ID NO: 10), relative to I-Zm.DnaK:1. The differences in expression imparted by I-Zm.GSI197.nno:1 (SEQ ID NO: 10), relative to I-Zm.DnaK:1, can be very useful where lower leaf and higher flower/anther expression is desired. Molecular analysis of the intron splice sites demonstrated consistent processing of the synthetic intron, I-Zm.GSI197.nno:1 (SEQ ID NO: 10).

Example 6

Analysis of the Effect on GUS Expression by the Synthetic 3' UTRs T-Zm.GST9.nno:2, T-Zm.GST18.nno:2, and T-Zm.GST43.nno:1, and the native T-Sb.Nltp4-1:1:2 in Stably Transformed 01DKD2 Variety Corn Plants Corn plants were transformed with a vector, specifically a plant expression vector containing test regulatory elements driving expression of the β-glucuronidase (GUS) transgene. The resulting plants were analyzed for GUS protein expression, to assess the effect of the selected regulatory element on expression.

Corn plants were transformed with plant GUS expression constructs. The regulatory elements were cloned into a base plant expression vector using standard methods known in the art. The resulting plant expression vectors contained a left border region from *Agrobacterium tumefaciens* (B-AGRtu.left border), a first transgene selection cassette used for selection of transformed plant cells that confers resistance to the herbicide glyphosate; a second transgene cassette to assess the activity of the 3' UTR regulatory elements, which comprised the EXP EXP-CaMV.35S (SEQ ID NO:21), operably linked 5' to the intron, I-Zm.DnaK:1 (SEQ ID NO:22), operably linked 5' to a synthetic coding sequence designed for expression in a plant cell encoding β-glucuronidase (GUS, GOI-Ec.uidA+St.LS1.nno:1, SEQ ID NO:20) containing a processable intron derived from the potato light-inducible tissue-specific ST-LS1 gene (Genbank Accession: X04753), operably linked 5' to a 3' termination region; and a right border region from *Agrobacterium tumefaciens* (B-AGRtu.right border). Three test expression vectors comprised the 3' UTRs T-Zm.GST9.nno:2 (SEQ ID NO: 13), T-Zm.GST18.nno:2 (SEQ ID NO: 14), or T-Zm.GST43.nno:1 (SEQ ID NO:26) operably linked to the GUS coding sequence. An additional test expression vector comprised the native 3' UTR T-Sb.Nltp4-1:1:2 (SEQ ID NO: 19) operably linked to the GUS coding sequence, and was used to compare expression between native and synthetic 3' UTRs.

Corn variety 01DKD2 plant cells were transformed using the binary transformation vector constructs described above by *Agrobacterium*-mediated transformation, as is well known in the art. The resulting transformed plant cells were induced to form whole corn plants.

Qualitative and quantitative GUS analysis was used to evaluate expression element activity in V4 leaf and root tissues of the transformed plants and was performed as described above in Example 3. The effect of the synthetic 3' UTRs was assessed through comparison to the effect of expression from the 3' UTR T-Sb.Nltp4-1:1:2 (SEQ ID NO: 19). The resulting transcripts were analyzed to determine if proper termination had occurred and that there was no read through of the transcript. One method to assess if there was read through was through the use of amplification of transcript cDNA using an amplification primer corresponding to a portion of the T-DNA border sequence that is 3' to the 3' UTR. The mean GUS expression of plants transformed with the four constructs comprising T-Zm.GST9.nno:2 (SEQ ID NO: 13). T-Zm.GST18.nno:2 (SEQ ID NO:14), T-Zm.GST43.nno:1 (SEQ ID NO:26), and T-Sb.Nltp4-1:1:2 (SEQ ID NO: 19) is provided in Table 10.

TABLE 10

Mean quantitative GUS expression in stably transformed 01DKD2 variety corn plants from constructs comprising three different 3' UTRs.

| Stage | Organ | T-Sb.Nltp4-1:1:2 (SEQ ID NO: 19) | T-Zm.GST9.nno:2 (SEQ ID NO: 13) | T-Zm.GST18.nno:2 (SEQ ID NO: 14) | T-Zm.GST43.nno:1 (SEQ ID NO: 26) |
|---|---|---|---|---|---|
| V4 | Leaf | 350 | 684 | 423 | 113 |
|    | Root | 778 | 924 | 810 | 883 |

As can be seen in Table 10, both T-Zm.GST9.nno:2 (SEQ ID NO: 13) and T-Zm.GST18.nno:2 (SEQ ID NO: 14) enhanced GUS expression driven by EXP-CaMV.35S operably linked I-Zm.DnaK:1, relative to the 3' UTR, T-Sb.Nltp4-1:1:2. GUS expression in plants comprising T-Zm.GST9.nno:2 (SEQ ID NO: 13) was higher than plants comprising T-Zm.GST18.nno:2. T-Zm.GST43.nno:1 (SEQ ID NO:26) enhanced GUS expression in the V4 root relative to the T-Sb.Nltp4-1:1:2, but attenuated expression in the V4 leaf. Analysis of the GUS transcripts from all four constructs demonstrated proper termination of the transcript and no evidence of read through in the resulting GUS transcripts. The 3' UTRs T-Zm.GST9.nno:2 (SEQ ID NO: 13). T-Zm.GST18.nno:2 (SEQ ID NO: 14), and T-Zm.GST43.nno:1 (SEQ ID NO:26) operate in a similar manner as native 3' UTRs and demonstrated modulation of GUS expression, relative to the native 3' UTR T-Sb.Nltp4-1:1:2. All four synthetic 3' UTRs and the additional native 3' UTR T-Sb.Nltp4-1:1:2 provide a range of expression values that are useful in fine-tuning expression in stably transformed corn plants.

Example 7

Enhancer Elements Derived from the Regulatory Elements

Enhancers are derived from the promoter elements presented as SEQ ID NOs:2 and 7. The enhancer elements may be comprised of one or more cis regulatory elements that when operably linked 5' or 3' to a promoter element, or operably linked 5' or 3' to additional enhancer elements that are operably linked to a promoter, can enhance or modulate expression levels of a transcribable DNA molecule, or provide expression of a transcribable DNA molecule in a specific cell type or plant organ or at a particular time point in development or circadian rhythm. Enhancers are made by removing the TATA box or functionally similar elements and any downstream sequence from the promoters that allow transcription to be initiated from the promoters presented as SEQ ID NOs:2 and 7 or fragments thereof.

The TATA box in plant promoters is not as highly conserved as in some other eukaryotic organisms. Therefore, in order to define a fragment as an enhancer, one first must identify the transcriptional start site (TSS) of the gene, wherein the 5' UTR is first transcribed. An enhancer derived from the synthetic promoter. P-Zm.GSP850.nno:4 (SEQ ID NO:2) could comprise nucleotides 1 through 418 of SEQ ID NO:2, resulting in the synthetic enhancer, E-Zm.GSP850 (SEQ ID NO: 17). An enhancer derived from the synthetic promoter. P-Zm.GSP990.nno:2 (SEQ ID NO:7) could comprise nucleotides 1 through 416 of SEQ ID NO:7, resulting in the synthetic enhancer. E-Zm.GSP990 (SEQ ID NO: 18). Enhancers derived from the promoters may comprise fragments of SEQ ID NOs:17 and 18, or duplications of SEQ ID NOs:17 and 18 or their respective fragments. The effectiveness of the synthetic enhancers derived from the synthetic promoters is empirically determined by building a chimeric transcriptional regulatory element comprising fragments derived from either the synthetic promoters P-Zm.GSP850.nno:4 (SEQ ID NO:2) or P-Zm.GSP990.nno:2 (SEQ ID NO:7), which is operably linked to a promoter and leader and used to drive expression of a transcribable DNA molecule such as GUS in stable or transient plant assay.

Further refinement of the enhancer element may be required and is validated empirically. In addition, position of the enhancer element relative to other elements within a chimeric transcriptional regulatory element is also empirically determined, since the order of each element within the chimeric transcriptional regulatory element may impart different effects, depending upon the relative positions of each element. Some promoter elements will have multiple TATA box or TATA box-like elements and potentially multiple transcription start sites. Under those circumstances, it may be necessary to first identify where the first TSS is located and then begin designing enhancers using the first TSS to prevent the potential initiation of transcription from occurring within a putative enhancer element.

Enhancer elements, derived from the promoter elements presented as SEQ ID NOs:2 and 7, are cloned using methods known in the art to be operably linked 5' or within a promoter element, or operably linked 5' or 3' to additional enhancer elements that are operably linked to a promoter. Alternatively, enhancer elements can be cloned, using methods known in the art, to provide a larger enhancer element that is comprised of two or more copies of the enhancer and cloned using methods known in the art to be operably linked 5' or 3' to a promoter element, or operably linked 5' or 3' to additional enhancer elements that are operably linked to a promoter producing a chimeric transcriptional regulatory element. Enhancer elements derived from promoters derived from genes from multiple genus organisms can be operably linked to the enhancers derived from the synthetic promoters.

A GUS expression plant transformation vector may be constructed using methods known in the art similar to the construct described in Example 3 in which the resulting plant expression vectors contain a left border region from *Agrobacterium tumefaciens* (B-AGRtu.left border), a first transgene selection cassette used for selection of transformed plant cells that confers resistance to the herbicide glyphosate; and a second transgene cassette to test the enhancer element comprised of the enhancer element operably linked 5' or 3' to a promoter element or operably linked 5' or 3' to additional enhancer elements that are in turn operably linked to a promoter which is operably linked 5' to a leader element, operably linked 5' to an intron element, operably linked to a coding sequence for β-glucuronidase (GOI-Ec.uidA+St.LS1.nno:1, SEQ ID NO:20) containing a processable intron derived from the potato light-inducible tissue-specific ST-LS1 gene (Genbank Accession: X04753), operably linked to a V termination region from the *Oryza sativa* Lipid Transfer Protein-like gene (T-Os.LTP:1, SEQ ID NO:23); and a right border region from *A. tumefaciens* (B-AGRtu.right border). The resulting plasmids are used to transform corn plants or other monocot genus plants by the methods described above. Alternatively, protoplast cells derived from corn or other monocot genus plants are transformed using methods known in the art to perform transient assays GUS expression driven by a regulatory element comprising one or more enhancers is evaluated in stable or transient plant assays to determine the effects of the enhancer element on expression of a transcribable DNA molecule. Modifications to one or more enhancer elements or duplication of one or more enhancer elements may be performed based upon empirical experimentation and the resulting gene expression regulation that is observed using each regulatory element composition. Altering the relative positions of one or more enhancers in the resulting regulatory or chimeric regulatory elements may affect the transcriptional activity or specificity of the regulatory or chimeric regulatory element and is determined empirically to identify the best enhancers for the desired transgene expression profile within the corn plant or other genus plant.

Having illustrated and described the principles of the present invention, it should be apparent to persons skilled in the art that the invention can be modified in arrangement and detail without departing from such principles. We claim all modifications that are within the spirit and scope of the claims. All publications and published patent documents cited herein are hereby incorporated by reference to the same extent as if each individual publication or patent application is specifically and individually indicated to be incorporated by reference.

What is claimed is:

1. A recombinant DNA molecule comprising a DNA sequence selected from the group consisting of:
   a) a sequence with at least 95 percent sequence identity to SEQ ID NO:2;
   b) a sequence comprising SEQ ID NO:2; and
   c) a fragment comprising at least 200 contiguous nucleotides of SEQ ID NO:2, wherein the fragment has gene-regulatory activity;
   wherein said DNA sequence is operably linked to a heterologous transcribable DNA molecule.

2. The recombinant DNA molecule of claim 1, wherein said sequence comprises at least 97 percent sequence identity to the DNA sequence of SEQ ID NO:2.

3. The recombinant DNA molecule of claim 1, wherein said sequence comprises at least 99 percent sequence identity to the DNA sequence of SEQ ID NO:2.

4. The recombinant DNA molecule of claim 1, wherein the DNA sequence comprises gene regulatory activity.

5. The recombinant DNA molecule of claim 1, wherein the heterologous transcribable DNA molecule comprises a gene of agronomic interest.

6. The recombinant DNA molecule of claim 5, wherein the gene of agronomic interest confers herbicide tolerance in plants.

7. The recombinant DNA molecule of claim 5, wherein the gene of agronomic interest confers pest resistance in plants.

8. The recombinant DNA molecule of claim 1, wherein the heterologous transcribable DNA molecule encodes a dsRNA, an miRNA, or a siRNA.

9. A transgenic plant cell comprising a recombinant DNA molecule comprising a DNA sequence selected from the group consisting of:
   a) a sequence with at least 95 percent sequence identity to SEQ ID NO:2;
   b) a sequence comprising SEQ ID NO:2; and
   c) a fragment comprising at least 200 contiguous nucleotides of SEQ ID NO:2, wherein the fragment has gene-regulatory activity;
   wherein said DNA sequence is operably linked to a heterologous transcribable DNA molecule.

10. The transgenic plant cell of claim 9, wherein said transgenic plant cell is a monocotyledonous plant cell.

11. The transgenic plant cell of claim 9, wherein said transgenic plant cell is a dicotyledonous plant cell.

12. A transgenic plant, or part thereof, comprising the recombinant DNA molecule of claim 1.

13. A progeny plant of the transgenic plant of claim 12, or a part thereof, wherein the progeny plant or part thereof comprises said recombinant DNA molecule.

14. A transgenic seed, wherein the seed comprises the recombinant DNA molecule of claim 1.

15. A method of producing a commodity product comprising obtaining a transgenic plant or part thereof according to claim 12 and producing the commodity product therefrom.

16. The method of claim 15, wherein the commodity product is seeds, processed seeds, protein concentrate, protein isolate, starch, grains, plant parts, seed oil, biomass, flour or meal.

17. A method of expressing a transcribable DNA molecule comprising obtaining a transgenic plant according to claim 12 and cultivating the plant, wherein the transcribable DNA is expressed.

* * * * *